(12) United States Patent
Heinze et al.

(10) Patent No.: US 6,915,254 B1
(45) Date of Patent: Jul. 5, 2005

(54) AUTOMATICALLY ASSIGNING MEDICAL CODES USING NATURAL LANGUAGE PROCESSING

(75) Inventors: Daniel T. Heinze, San Diego, CA (US); Mark L. Morsch, San Diego, CA (US)

(73) Assignee: A-Life Medical, Inc., San Diego, CA (US)

( * ) Notice: Subject to any disclaimer, the term of this patent is extended or adjusted under 35 U.S.C. 154(b) by 0 days.

(21) Appl. No.: 09/364,930

(22) Filed: Jul. 30, 1999

Related U.S. Application Data

(60) Provisional application No. 60/094,688, filed on Jul. 30, 1998.

(51) Int. Cl.[7] .......................... G06F 17/27; G06F 17/30
(52) U.S. Cl. .............................. 704/9; 704/257; 705/2; 705/3; 707/2; 382/225
(58) Field of Search .............................. 704/9, 257, 1, 704/10; 705/2, 3; 382/225; 707/2, 531, 532, 533, 534; 706/45, 47, 50, 53, 54, 55

(56) References Cited

U.S. PATENT DOCUMENTS

| | | | | |
|---|---|---|---|---|
| 5,483,443 A | | 1/1996 | Milstein et al. ................. | 705/3 |
| 5,594,638 A | * | 1/1997 | Iliff .............................. | 705/3 |
| 5,619,709 A | * | 4/1997 | Caid et al. .................... | 707/532 |
| 5,675,819 A | * | 10/1997 | Schuetze ........................ | 707/2 |
| 5,680,511 A | * | 10/1997 | Baker et al. ................. | 704/257 |
| 5,794,178 A | * | 8/1998 | Caid et al. ...................... | 704/9 |
| 5,809,476 A | | 9/1998 | Ryan .............................. | 705/2 |
| 5,873,056 A | * | 2/1999 | Liddy et al. .................... | 704/9 |
| 6,055,494 A | | 4/2000 | Friedman ........................ | 704/9 |
| 6,137,911 A | * | 10/2000 | Zhilyaev ...................... | 382/225 |
| 6,182,029 B1 | | 1/2001 | Friedman ........................ | 704/9 |

OTHER PUBLICATIONS

Friedman, et al.: "Natural Language Processing in an Operational Clinical Information System", Nautral Language Engineering, col. 1, May 1995, pp. 83–108.*

Zingmond and Lenert, Monitoring Free-Text Data Using Medical Language Processing, Computers and Biomedical Research 26, pp. 467–481, 1993, Stanford, CA.

Lehnert, Soderland, Aronow, Feng, and Shmueli, Inductive Text Classification for Medical Applications, Brookline, MA.

(Continued)

Primary Examiner—Patrick N. Edouard
Assistant Examiner—Lamont Spooner
(74) Attorney, Agent, or Firm—Fish & Richardson P.C.

(57) ABSTRACT

A programmed implementation for automatically assigning medical codes (including diagnosis, procedure, and level of service—i.e., evaluation and management (EM)—codes) to computer readable physician notes using natural language processing. A system allows hospitals, physician management groups, and medical billing companies to automatically determine and assign the medical codes that are the basis of reimbursement for medical services. The proposed implementation can be in place of human medical coders who otherwise would be employed to determine and assign these codes. Implementation requires only minor modifications to the traditional data-flow and allows for major improvements in throughput and timeliness of billing. Further, the present scheme enables the collection of other demographic and clinical information that resides in physician notes, but that are currently too expensive and time consuming to extract by means of a human workforce.

49 Claims, 11 Drawing Sheets

OTHER PUBLICATIONS

Larkey and Croft, Automatic Assigment of ICD9 Codes to Discharge Summaries, Amherst, MA.

Sneiderman, Rindflesch, and Aronson, Finding the Findings: Identification of Findings in Medical Literature Using Restricted Natural Language Processing, 1996, Bethesda, MD.

Aronow, Cooley, and Soderland, Automated Identification of Episodes of Asthma Exacerbation for Quality Measurement in a Computer–Based Medical Record, Brookline, MA and Amherst, MA.

Croft, Callan, and Aronow, Effective Access to Distributed Heterogeneous Medical Text Databases, 1995, Amherst, MA.

Aronow, Soderland, Feng, Croft, and Lehnert, Automated Classification of Encounter Notes in a Computer Based Medical Record, Amherst, MA.

Aronow and Shmueli, A PC Classifier of Clinical Text Documents: Advanced Information Retrieval Technology Transfer, Amherst, MA.

Aronow and Feng, Ad–Hoc Classification of Electronic Clinical Documents, 1997, Amherst, MA.

Soderland, Aronow, Fisher, Aseltine and Lehnert Machine Learning of Text Analysis Rules for Clinical Records, Amherst, MA and Brookline, MA.

Yang and Chute, An Application of Least Squares Fit Mapping to Clinical Classification, $16^{th}$ Annual Symposium on Computer Application in Medical Care, pp. 460–464, 1993, Rochester, Minnesota.

Ranum, Knowledge Base Understanding of Radiology Text, $12^{th}$ Annual Symposium on Computer Application in Medical Care, pp. 141–145, 1988, Rochester Minnesota.

Sager, Lyman, Nhan, and Trick, Automatic Encoding into SNOMED III: A Preliminary Investigation, $18^{th}$ Annual Symposium on Computer Application in Medical Care, pp. 230–234, 1994, New York, NY.

Lenert and Tovar, Automated Linkage of Free–Text Descriptions of Patients with a Practice Guideline, $17^{th}$ Annual Symposium on Computer Application in Medical Care, pp. 274–278, 1993, Stanford, CA.

Sager, Lyman, Bucknall, Nhan, and Trick, Natural Language Processing and the Representation of Clinical Data, Journal of the American Medical Information Association, vol. No. 2, Mar./Apr. 1994, New York, NY.

* cited by examiner

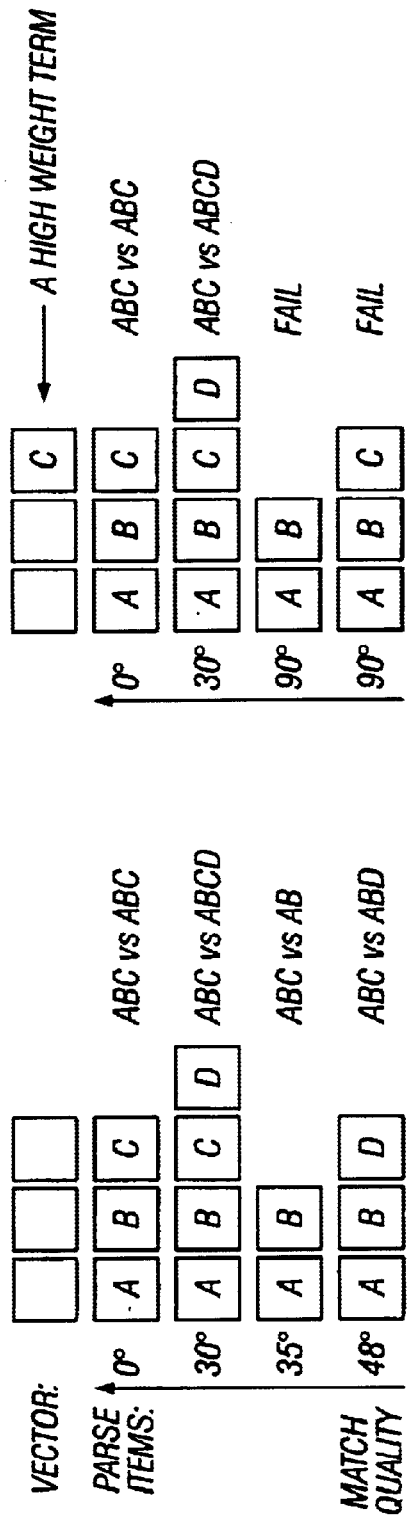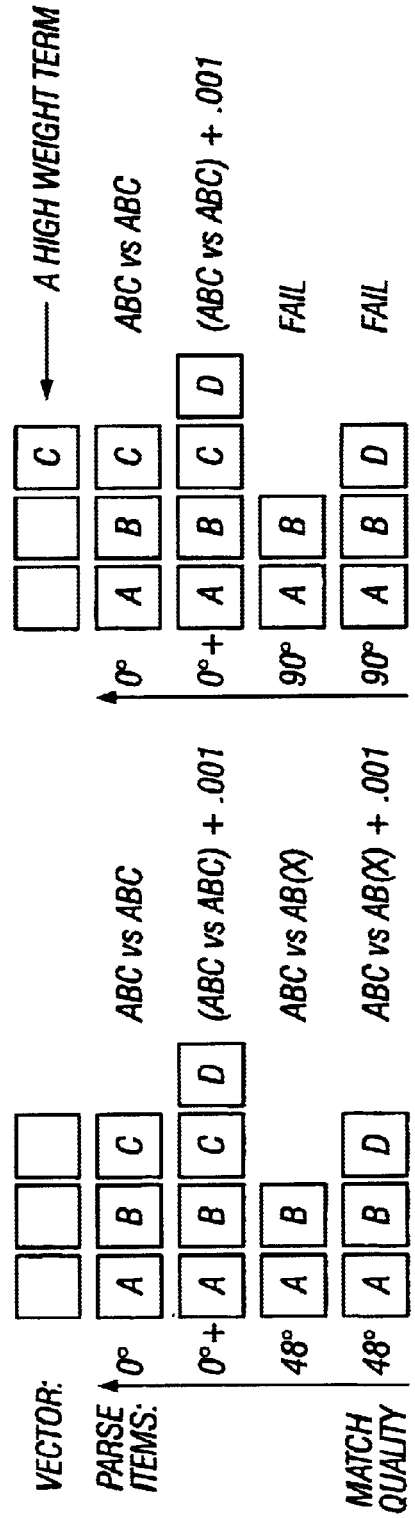
FIG. 5B
FIG. 5C

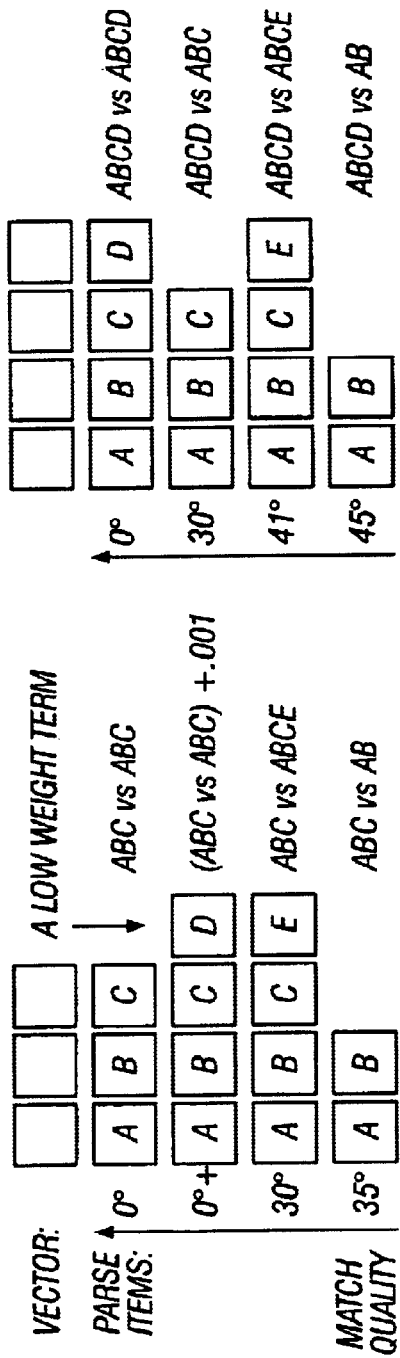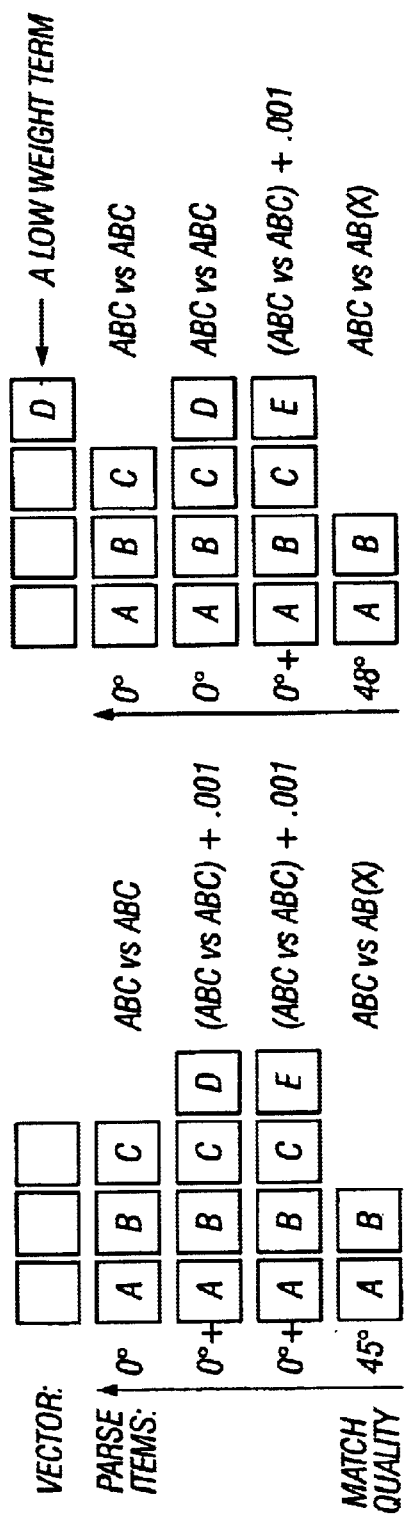
FIG. 5D
FIG. 5E

AUTOMATICALLY ASSIGNING MEDICAL CODES USING NATURAL LANGUAGE PROCESSING

CLAIM OF PRIORITY

This application claims priority under 35 USC §119(e) to U.S. Patent Application Ser. No. 60/094,688, filed Jul. 30, 1998.

TECHNICAL FIELD

The invention relates to computer natural language processing (NLP), and more particularly, to a system and method of using NLP to automatically assign medical codes to diagnoses and procedures performed by physicians for billing purposes and the like.

BACKGROUND

Three broad areas of application have emerged over the years in computer natural language processing (NLP). These include text translation, document retrieval and routing, and information extraction. Practical text translation systems work primarily on the basis of pattern matching and mapping. Retrieval and routing systems are based primarily on keyword matching augmented by statistical and proximity measures and word manipulations based on morphology and synonymy. Information extraction systems vary more widely in terms of implementation algorithms. Some systems are based purely on keywords, statistics and pattern matching. However, most systems have some level of linguistic processing capability.

In the area of medical NLP, several academic research systems have been designed and built for the purpose of processing the information in physician notes. One area of basic research is classification of medical terms based on definition in context. Medical terminology, as does all natural language components, has ambiguities. The study of how to resolve ambiguities based on contextual clues is an important area of basic research.

Typical medical coding applications function simply as computerized look-up tools. Search terms retrieve candidate codes from on-line versions of standard coding references. Search terms are entered into pre-contextualized slots to further focus the search and improve accuracy. Coding from a full narrative of physician notes, however, is not yet available or even possible by conventional coding applications.

Medical applications related to processing of the full narrative of physician notes are largely related to retrieval and routing. For example, U.S. Pat. No. 5,809,476 to Ryan describes the use of NLP to apply diagnosis and procedure codes to physician notes. However, traditional NLP approaches for generating medical codes are inefficient and inaccurate. To survive and thrive in today's medical climate, medical records coding needs to produce reliable, consistent results.

Many modern solutions cannot parse large documents based on document structure. In particular, most cannot parse sentences in a manner that would permit learning of syntactic clues that affect term combination and disambiguation. In many systems, an overall approach for accepting or rejecting potential term combinations is lacking.

At present, no known solution exists for identifying the presence of relevant information in physician notes that an NLP system may be able to use for purposes of interpretation or extraction of information.

Also, no capability is known to exist to identify who, in the context of a physician's narrative, is describing a symptom, diagnosis, or procedure, and then use such information.

No known solution makes an assessment of the level of medical service based on the application of established rules for medical coding to the raw content of a physician's note.

Generally, work-flow evaluations are incomplete in that no solution (1) integrates demographic information with a physician note, (2) ensures completeness of a transcription of a physician note; and/or (3) provides capability for integrating human input to resolve problems of ambiguity or incomplete information.

The capability to attribute a statement to the correct source and to determine the affirmation or denial status of a statement is critical for proper and accurate billing (or even clinical) purposes. Also, medical service codes are based on factors other than the particular diagnosis or procedure(s) performed, such as for example, past medical history, family medical history, social habits of the patient, and extent and nature of the physical examination.

Accordingly, the inventors have determined that it is desirable to be able to automate medical diagnosis, procedure, and level of service (also known as evaluation and management (EM)) coding in a more efficient manner to provide a more reliable indicator of physician notes.

SUMMARY

The invention automatically assigns medical codes to physician notes using natural language processing (NLP). The invention allows hospitals, physician management groups, and medical billing companies to automatically determine and assign medical codes for reimbursement of medical services. Such codes include standard ICD and CPT codes. The medical billing industry is thus capable of becoming significantly modernized by reducing the need for human intervention, improving consistency of coding, increasing throughput, and decreasing reimbursement time.

The invention is implemented by way of a computer system which allows for input of physician notes and attendant demographic information as well as output of coded results (for example, in the form of an interactive graphical user interface, a printed insurance claims form, or as an electronic record suitable for input to a computerized billing system).

In one aspect, the invention includes a method of automatically interpreting a transcribed note using vector processing to generate associated codes comprising the steps of segmenting the transcribed note into a plurality of segments; applying morphing, parsing and semantic analysis to the segments to generate a normalized file having a standardized form with parse items; identifying first type matches between parse items of the normalized file and a plurality of standard knowledge vectors, the first type matches being indicative of associations to a single code; generating associated codes at least on the basis of the first type matches and on the basis of natural language processing rules applied to the parse items; and outputting the generated associated codes.

The invention takes advantage of the latest in computing technology to accept input physician notes as any of a wide variety of formats. The input origins may be a word processor, optical character recognizer (OCR) or automated speech recognition (ASR). Each physician note is archived in its original form for later retrieval. Physician notes are reformatted by the medical provider and/or a provider's transcription service so as to normalize the layout of the file. Once normalized, the data file is processed by an NLP engine. The NLP engine makes separate passes over the file to code diagnoses, procedures, and evaluation and management (EM) level.

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 5(a)–5(e) are flow diagrams showing the vector comparison process.

Like reference numbers and designations in the various drawings indicate like elements.

DETAILED DESCRIPTION

Overview

Figure 1:
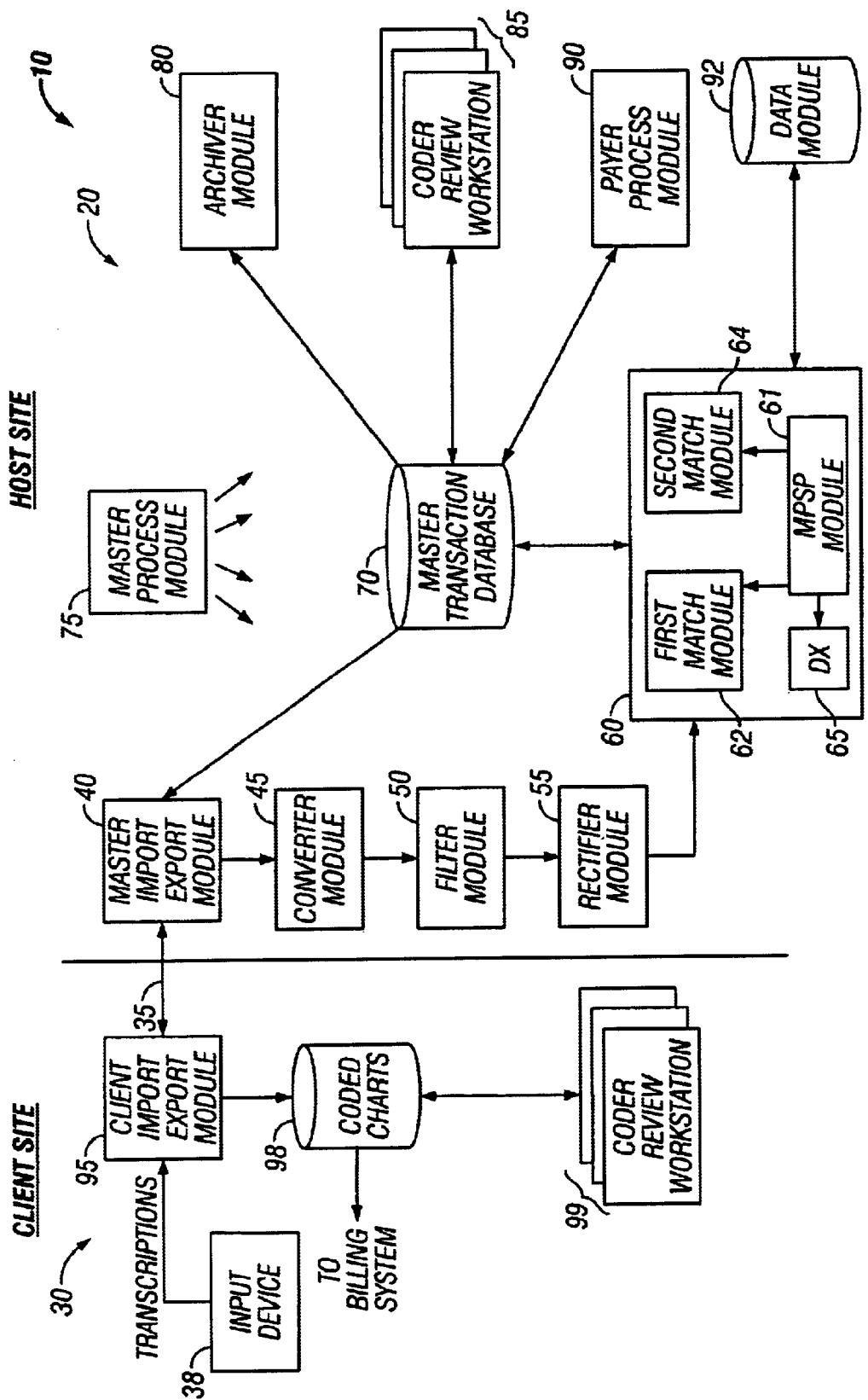
FIG. 1 is an overall architecture diagram of a code generating system in accordance with the present invention.

The invention automatically assigns medical codes (including diagnosis, procedure, and level of service—i.e., evaluation and management (EM)—codes) to computer readable physician notes. The invention allows hospitals, physician management groups, and medical billing companies to automatically determine and assign medical codes that are the basis of reimbursement for medical services. The preferred implementation can replace human medical coders who otherwise would be employed to determine and assign these codes. Implementation requires only minor modifications to the traditional data-flow and allows for major improvements in throughput and timeliness of billing. Further, the preferred embodiment enables the collection of demographic and clinical information that resides in physician notes, but which is currently too expensive and time consuming to extract by means of a human workforce.

It is contemplated that the invention may be implemented, for example, on standard desktop computers running a conventional operating system (e.g., Windows NT or UNIX).

For purposes of the description herein, a client is a billing company or billing department for which medical coding of physician notes is being performed. Demographics includes any information detailing when, where, and by whom a patient was treated along with the patient name, a unique identifier, payer information, and the like. Clinical information or data includes diagnoses and surgical procedures, as well as information about a patient's medical history, medications and dosages, and is generally data that goes into determining diagnosis, procedure and EM codes. A physician note (or, simply, "note") is a physician generated record of a physician-patient encounter. Such notes may be handwritten, recorded by audio dictation systems, or directly input into a computer (e.g., by means of a general word processing program or a dedicated medical records program). A payer is the party generally responsible for payment of a medical bill, usually an insurance company. A provider is an organization that provides medical services. In an emergency care situation, the provider is typically a hospital or clinic. The invention is adaptable to accept a physician's note in any of a wide variety of formats. For example, the note may be a word processor generated file, a file generated from a printed record by an optical character recognizer (OCR), or the output of an automated speech recognition (ASR) system. The note may be archived in its original form. Alternately, copies may be automatically converted to plain text format for internal processing. As shall be described in greater detail, each note is normalized to a format that meets the specifications of a medical provider and/or its transcription service. The normalized file is then typically processed by a central natural language processing (NLP) engine.

In the preferred embodiment, the NLP engine makes separate passes over each normalized file as part of the process of coding diagnoses, procedures, and EM level. For every pass one or more different segments of the file in context are identified, then further normalized. Normalizing may involve, for example, changing spacing between words and around punctuation marks to a single blank space (as opposed to no space before punctuation marks, and in various combinations of blank spaces, tabs, carriage returns and form feeds between words and after punctuation marks).

The NLP engine then morphs words in the normalized file to transform standard, predefined morphological forms. Morphology algorithms attempt to re-define data into non-ambiguous standardized forms.

Once morphed, a bottom-up linguistic parse is performed on each sentence of the document. Bottom-up parsing segments the document into parse items, such as sentences, clauses, and phrases. This is useful because physician notes tend to lack grammatically proper sentence structure. During the parse, negated sentences, clauses and phrases are also marked. Cardinal and ordinal numbers are identified, as are various locative constructs and statements of magnitude. In any event, regardless of original form, each note is transformed into a computer-readable "transcribed note".

Based on the bottom-up parse, phrases, clauses, and sentences are matched individually and in combination against knowledge-based vectors stored in a database. Millions of these vectors collectively represent a body of medical and coding knowledge. The vectors are the descriptions of diagnoses and procedures stored in one of three forms, i.e., "is-a", "synonymy", and "part/whole" type relations.

The medical and coding knowledge represented by the vectors comprise the universe of types and relations, for example, between body parts and regions, infectious organisms, poisons, hazardous substances, drugs, and medicinals.

The matching of vectors to parsed data is performed at the phrase, clause, sentence, and adjacent sentence levels. A resolver—a type of knowledge based tool—intelligently maps information within and across sections of the normalized file. The resolver ultimately applies high-level medical coding rules to produce a complete set of diagnosis, procedure, and EM level codes.

The resolver is adaptable to apply rules that are specific to the particular provider and payer associated with a physician note. The resolver thus includes a knowledge base of severity and reimbursement values per code, code ordering rules, code mappings specific to particular payers, and knowledge of codes that are not billed by particular providers or billed to particular payers. The resolver also associates the diagnosis codes with the appropriate procedure and EM level codes.

In addition to the vectors that define codes of which the NLP engine has complete knowledge, there are vectors that define codes for which knowledge is incomplete. (This is like a human coder who is able to recognize that the physician is describing a diagnosis, but who may not fully understand terms the physician is using). The NLP engine includes a set of knowledge vectors that broadly define the language of the entire set of diagnoses that can be coded. These vectors—termed "semi-knowledge vectors"—are not sufficiently detailed to permit accurate coding of specific diagnoses in all instances. Each semi-knowledge vector yields a range of possible diagnosis codes when matched to information in the normalized file. When a match to a semi-knowledge vector occurs, the NLP engine checks whether an acceptable standard vector is also matched. When a standard vector is not matched, the physician note is flagged. The NLP engine may interactively prompt a human coder for additional information in an effort to gather information necessary to complete coding of the note.

A physician note is also flagged for further review by a human coder if the transcribed note contains certain codes that are known either to be insufficiently reliable or that require corroboration from other sources (e.g., nurse notes and/or hospital orders). While non-flagged documents eliminate the need for human coder interaction, flagged documents also improve system reliability and reduce coder interaction by directing a coder's attention only to those sections or portions of a physician note that are ambiguous.

The generated codes and associations for justification, and various pieces of demographic information are placed in an output record that can be displayed to an interactive graphical user interface for review and/or modification, printed as a billing form, stored as an (archived) computer file, or sent as electronic input to a third-party billing software system.

Basic Architecture and Data Flow

A high-level architectural block diagram of a medical coding system is depicted in FIG. 1. The complete medical coding system 10 for interpreting transcribed notes and generating associated codes may be represented in terms of data flow to/from a host site 20 from/to a client site 30.

Host site 20 includes Master Import/Export Module 40, Converter Module 25, Filter Module 50, Rectifier Module 55, NLP Engine 60, Master Transaction Database 70, Master Process Module 75, Archiver Module 80, host Coder Review Workstations (CRW) 85, and Payer Process Module 90. NLP Engine 60 further includes a Morphological, Parse and Semantic Processing (MPSP) module 61 coupled to first and second vector matching modules 62, 64. A data module 92 is coupled to NLP Engine 60, as shown. These modules together encapsulate a medical coding process described in detail further below in connection with FIGS. 2–8.

Client Site 30 is characterized by Client Import/Export Module 95, memory storage device 98 storing coded charts and records, and client Coder Review Workstations (CRW) 99.

The host site input data 35 includes a transcribed physician note, hereafter referred to as the note or notes, and patient demographic and clinical information. The demographic information and the clinical information may be contained in the note or in one or more separate records from the provider (e.g., a hospital, clinic or medical office). A note is initially produced when a physician uses an input device 38 to write, dictate or otherwise input a report regarding a physician-patient encounter. The report may have been transcribed by a transcriptionist, by a voice-recognition system, or by any other known means. The transcribed note may be stored on a computer in pure ASCII format, but is more typically created and stored in a word processor format.

Demographic and clinical information not found in the note is produced at the provider when a patient is registered. This information may be available in electronic format for direct import into the coding system or may be in paper form and require data entry at a computer terminal or by an OCR terminal.

Data flow to/from host site 20 facilitates the processing of incoming notes, clinical information, and demographic information, transformation and manipulation of that data, potential quality assurance review, and the final downloading of resulting data back to the client site 30 along with an internal archive process.

In a current preferred implementation, input data 35 comprising transcribed notes including clinical and demographic information is received from Client Import/Export Module 95 either in batch or in individual records. The input may be transferred using a variety of communication protocols such as TCP/IP or FTP.

Received data is processed by Master Import/Export Module 40. Module 40 includes a "landing zone" or data buffer. This is where the input data 35 is initially placed.

Converter Module 45 polls this landing zone for files to process and converts necessary files from any proprietary format (e.g., word processing) to a plain text file, such as ASCII text. Converter Module 45 then returns the records to the landing zone for processing by Filter Module 50. Converter Module 45 places the raw text into a new record in Master Transaction Database 70. Under Master Process Module Control 75, records in Database 70 are assigned unique IDs. Additional fields are not parsed out until after the filter module has completed. An indication is then generated when records are available for processing by the Filter Module 50.

Filter Module 50 reads records in Master Transaction Database 70 one at a time, extracting the header demographic information and performing cleanup. An initial entry into Master Transaction Database 70 is then made. Records may be keyed off a combination of the client source, date, patient name, medical record number, and like data.

Filter module 50, after cleaning up the data, creates a status of the record in Master Transaction Database 70 and saves the final processed text. An indication is then made when records are available for processing by Rectifier Module 55.

Rectifier Module 55 polls Master Transaction Database 70 for records to process and creates an internal result set of records that are ready for processing. This is typically based on a record being in the system long enough. Once the Rectifier Module 55 retrieves those records, it attempts to put certain partial, updated or addendum records together and re-insert them in the Master Transaction Database 70 as one record. An indication is then made that records are available for processing by appropriate medical coding algorithms generally hosted by NLP Engine 60.

Once the records are appended, they are available for medical coding. Rectifier Module 55 extracts the records one at a time and sends them to the NLP Engine 60. The host site 20 is then informed that the records were forwarded to the NLP Engine.

NLP Engine 30 reads the records in its landing zone and converts them to a format suitable for medical coding described in greater detail below. The records are then placed in a landing zone for processing by the underlying medical coding algorithms. The host site 20 is again informed when this step is done.

Under the control of Master Process Module 75, the MPSP module 61 and vector matching modules 62, 64 execute appropriate medical language processing and medical coding algorithms to generate processed records. The NLP Engine 30 polls the processed records, reads them, and places all of the result data records into the Master Transaction Database 70. Appropriate follow-up action is taken if further quality assurance review is necessary. The NLP Engine 30 may optionally include a data extractor module 65 coupled to the MPSP module to facilitate extracting demographic and clinical information that resides in physician notes.

Payer Process Module performs final transformations on the processed records when payer data is available. This data may have been made available as separate information received at the Master Import/Export Module 40, or be received as part of the original input data 35.

Records that have undergone medical coding and require no additional attention are stamped complete and archived. Non-complete records are stamped as needing quality assurance review and stored in the Master Transaction Database 70.

For those records requiring further attention, a quality assurance staff member working at one of the host CRWs 85 opens user queues that show a list of those records in the database needing processing and selects a record. The coder then edits the record within a host CRW 85 and forwards it back to the Master Transaction Database 70, where the record is stored until follow-up medical coding processing is taken.

For certain records stamped "incomplete" and not able to be processed by the quality assurance staff, no further processing is performed. These records are ultimately stamped as "uncodable" and returned to the client site 30 as such.

After either the medical coding process or the quality assurance staff processes all the records, the Master Import/Export Module 40 fetches them from the Master Transaction Database 70 and downloads them to the client site 30. Records that were processed and complete are identified and marked as ready for submission to a client billing system. Incomplete records are also identified as needing further quality assurance review at the client site.

The Client Master Import/Export Module 95 imports the downloaded records into, for example, a local SQL Server database. After the client's quality assurance staff validates them, all of the records can be automatically imported back into the client's billing system.

Human coders comprising the client quality assurance staff process any remaining records and trigger their export to the billing system.

Back at the host site 20, Archiver Module 80 runs at a regular time and archives all appropriate records off the Master Transaction Database 70.

Payer Process Module 90 works in the background creating accounts payable records and placing them in an export file for import to the client site billing system.

Medical Coding Process

Figure 2:
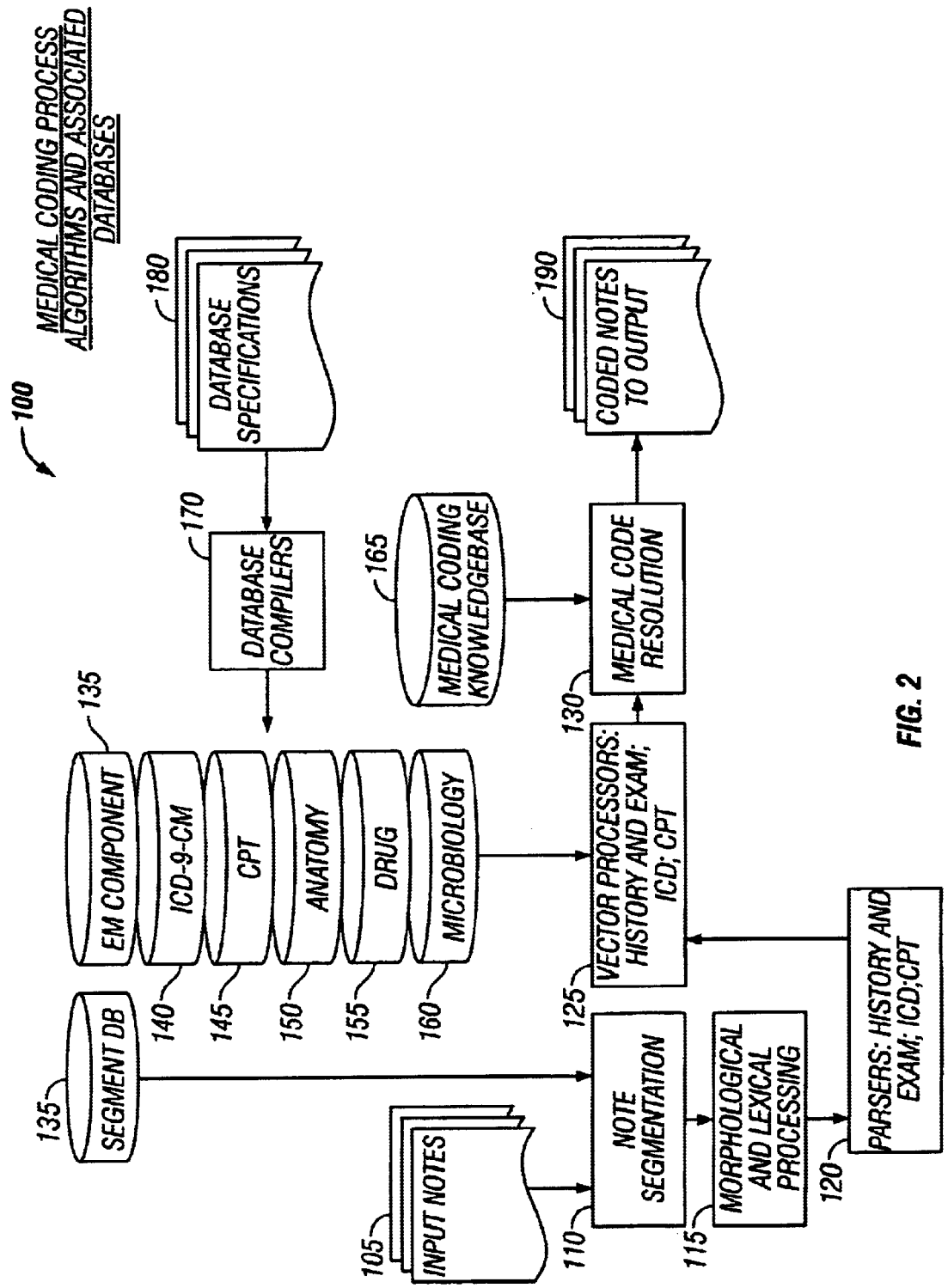
FIG. 2 is a block level diagram of the NLP medical coding engine.

FIG. 2 is an operational flow diagram of the medical coding process 100 performed by the various cooperating modules described above in connection with FIG. 1. The medical coding process is generally broken up into four sub-process stages. These stages collectively define a knowledge-based tool, hereafter referred to as a resolver. The resolver includes appropriate algorithms for performing note segmentation 110, morphological and lexical processing 115, parser processing 120, vector processing 125, and code resolution processing 130.

Note Segmentation

Note segmentation involves the processing of input notes 105 in a manner taking into account that for billing purposes such notes include certain information. For example, each note 105 typically is required to contain certain sections: the history of the present illness; an exam description; a description of the course of action/treatment; and a list of final diagnoses. Other sections may also be present. These include but are not limited to: chief complaint; review of systems; family, social and medical history; review and interpretation of lab work and diagnostic testing; consultation notes; and counseling notes. Because there is no uniform order or labeling for sections, the note segmentation algorithm must attempt to associate each paragraph of the note with one of the required or optional segment types. If all of the required sections cannot be identified, a note is flagged and submitted for human review and returned to the provider for completion as needed.

Thus, note segmentation generally involves processing input notes 105 to identify section headings. Once identified, these headings are categorized and the paragraphs falling within each section are associated with the correct section heading. Section headings provide context within which the associated paragraphs may be interpreted. For example, it is expected that the history of present illness will contain a description of a patient's symptoms including the context and setting of symptom onset and the duration and timing of the current symptoms. Automatic segmentation of the note is a two-step algorithmic process: (1) identification of possible section headings through lexical pattern matching, and (2) resolution and categorization of section headings using vector matching with marking of section extents.

During note segmentation, candidate section headings are identified using lexical patterns—specifically, regular expressions. Examples of three regular expressions used to identify possible section headings are shown below:

Pattern 1: ^[\t]*[A-Z][A-Za-z#_/\\-]+:

Pattern 2: [A-Z][A-Z#_/\\-]+:

Pattern 3: ^[\t]* [A-Z][A-Z#_/\\-]+

A list of candidate section headings is created by scanning each line of text in the physician note and comparing the scanned text against regular expressions similar to the three patterns shown above. A sequence of characters matching any of the patterns is copied into a list of candidate section headings. This list stores the section headings in the order they appear in the document along with the offsets, with respect to the original note, of the first and last characters of each section heading. The algorithm also identifies multiple section headings on a single line and a single section heading split across two lines.

The note segmentation algorithm resolves and categorizes sections using vector matching techniques. Vector matching is used in several components of the current medical coding implementation. The algorithms implementing the vector processing are described in greater detail below and in the accompanying appendices A and B.

During vector matching, a group of individual words are compared—by the first vector matching module 62 (see FIG. 1)—against a set of term vectors. Each term vector in turn consists of a group of words. The individual words of each term vector are compared against the source group of words. The number of words in common between the source group and a term vector determines a degree of similarity. A perfect match would exist when both the source group and the term vector have the same number of words and there is a one-to-one identity match for every word. The set of term vectors is also classified according to domain-dependent breakdown. A portion of the term vector database for section headings is shown below:

```
complaint:
    chief complaint |
    complaint
;
allergy:
    allergy |
    allergies |
    allergy medication |
    allergy to medication
;
system_review:
    review of systems |
    review of system |
    systems |
    ros
;
physical_exam:
    pe |
    physical examination |
    physicial examination |
    physical examintion |
    physical exam |
    physical findings |
    physical
;
```

The section categories are the terms prior to the colon in each grouping. Individual term vectors are separated by a vertical bar "|" following the section category. The vectors for one section category are terminated by a semicolon. Note, in the term vector for physical examination, the inclusion of common misspellings such as "physicial" and "examintion" for "physical" and "examination", respectively.

Figure 3:
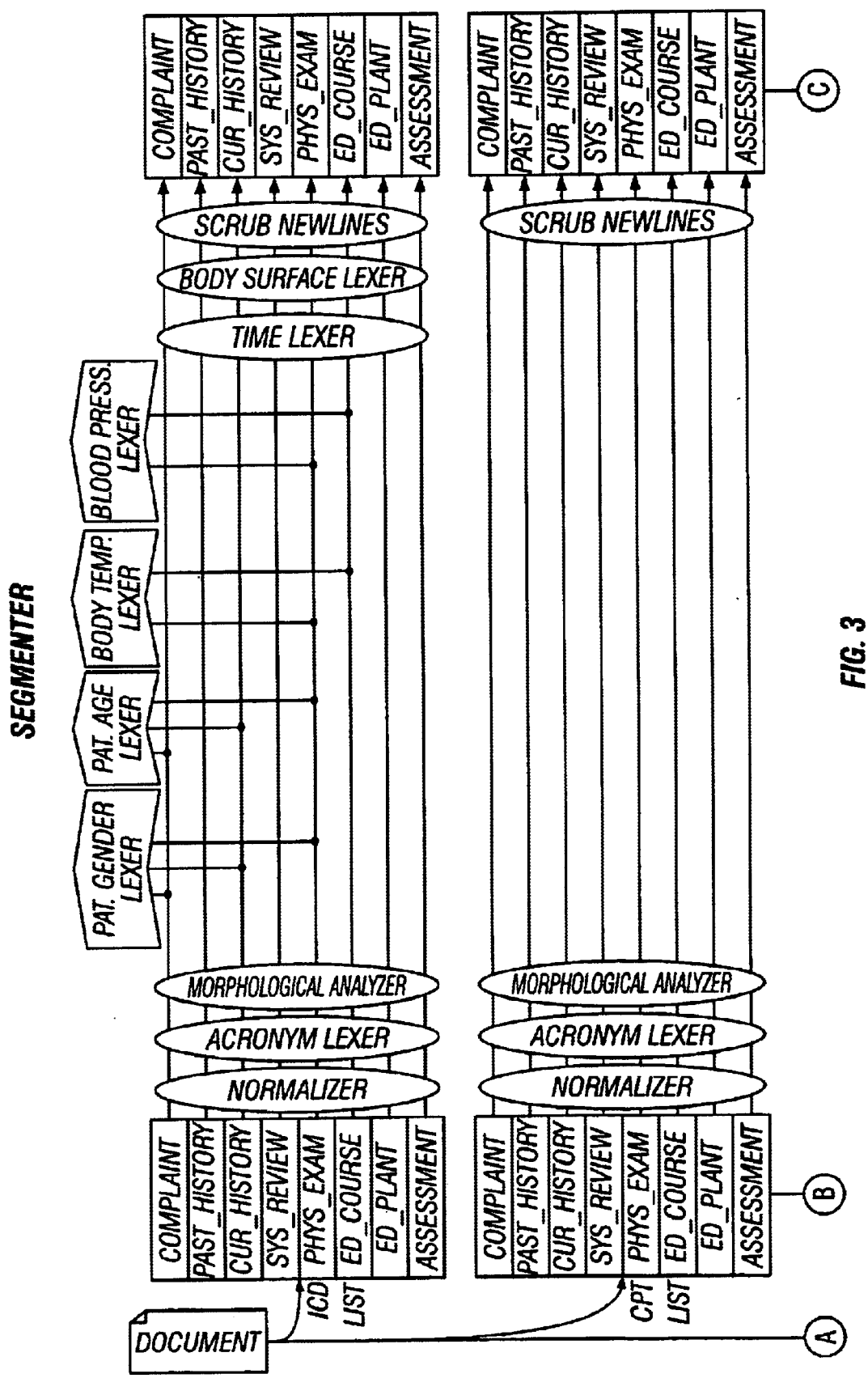
FIG. 3 is an operational flow diagram of a preferred segmenter.
Figure 3:
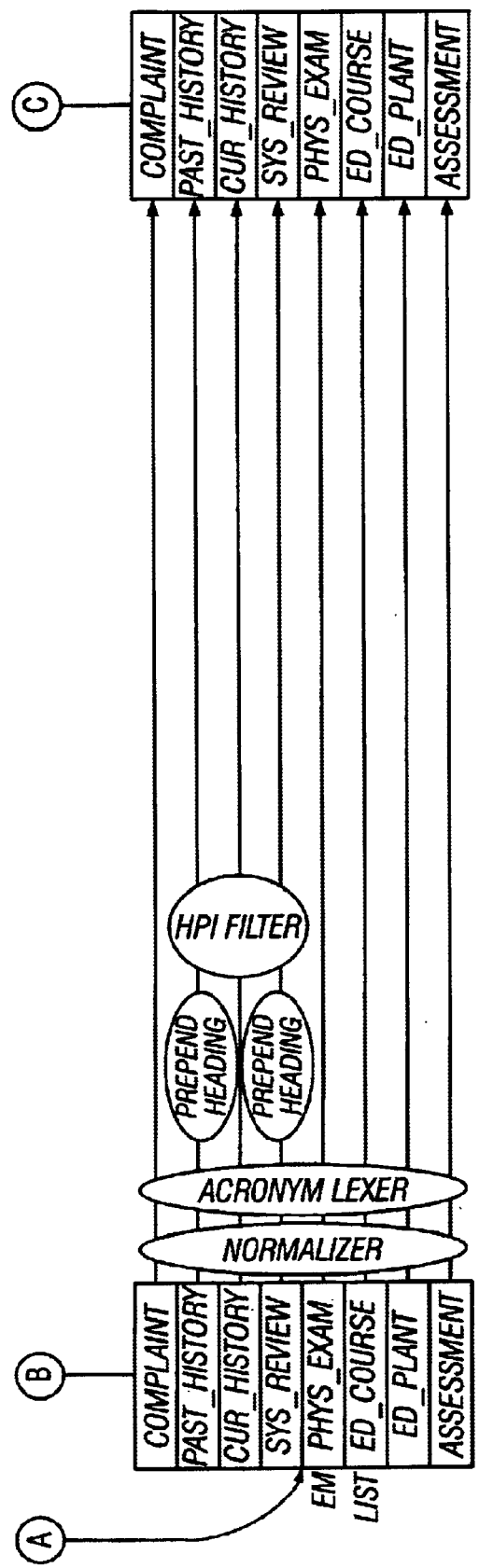

An exemplary note segmentation flow process is illustrated in FIG. 3. During note segmentation, each candidate section heading is compared against section-heading vectors in a segment database 135 using appropriate vector processing algorithms. The candidates that match are validated as confirmed section headings. All text characters from the end of the current section heading to the beginning of the next confirmed section heading in the note are considered one segment. Each segment includes a copy of the text making up the section, the section category, and the offsets of the first and last character in the segment with respect to the original note. This information is stored together in a data structure and placed on a list representing confirmed sections.

Morphological and Lexical Processing

After note segmentation 110, notes are forwarded for further processing. Morphological processing includes both word and phrase level processing to normalize word forms and phraseology. Such processing may include but is not limited to the following morphers:

1. Acronym: morphs acronyms to their full form or to some other unambiguous normal form—e.g., LLQ=>left lower quadrant (of abdomen).

2. Age: morphs statements of patient age to a label, a normal form consisting of an age scale (hours, days, weeks, months, years) and an integer.

3. Body surface: morphs statements regarding the extent of body surface affected by a condition to a label, a percentage represented as an integer, and a relative modifier (less than, equal, greater than)—e.g., "more than one-forth of the body surface"=>GT 25%.

4. Body temperature: morphs statements of body temperature to a label and a temperature as a real number normalized to the Fahrenheit scale.

5. Blood pressure: morphs statements of blood pressure to a label followed by the systolic pressure, a space, and the diastolic pressure each represented by an integer—e.g., "systolic pressure was 125 and dystolic 70"=>BP 125/70.

6. Cranial nerve: morphs statements regarding the cranial nerves to a label and a comma delimited list of integers representing the cranial nerves being referenced—e.g., "the first and third through fifth cranial nerves"=>CN 1, 3, 4, 5.

7. Gender: searches for the first statement of patient gender in the chief complaint and/or history segments of the note and places a gender label in an object for later reference—"the patient said she cut her . . . "=>GENDER_FEMALE.

8. HPI filter: serves several purposes in preparing the chief complaint and/or history sections for vector processing. Anatomical terms used in reference to other people (e.g., "the patient tripped over his friend's foot") or to inanimate objects (e.g., "the patient tripped on the foot stool") are morphed to a form that will not be confused with the patient's anatomy. References to old injuries and medical conditions are morphed to a form that will not be counted as a sign or symptom associated with the current illness (e.g. "the patient has a history of seizures" or "the patient had a TIA two years ago" verses "the patient experienced a seizure two hours ago" or "the patient presents with signs of a TIA". Statements related to time of onset are put in a normal form so that the date of onset can be calculated back from the date of service—e.g., if current date is Jul. 27, 1998 then "vomiting began two days ago"=>ONSET Jul. 25, 1998 2 DAYS. (These time-related morphs are further augmented by the operation of the Past time morpher; see item 12 below). Statements to the effect that the patient was at his/her place of employment at the time of onset are identified and differentiated from statements that merely say that the patient was working in some manner at the time of onset (e.g., "the patient was working in her garden . . . ").

9. Length: morphs statements of wound length to a normal form consisting of a modifier (less than, equal, greater than) a real number length, and a scale (inches, centimeters, etc.).

10. Word morphology: morphs synonyms, spelling variants and equivalent morphological forms of words to normal forms. This process is applied to both the vector databases and to the physician notes so that word forms are properly recognized.

11. Normalizer: morphs white space, punctuation, diacritical marks, and special characters to normal form.

12. Past time: provides two morphological functions relative to statements of past time events. Statements of duration are morphed to a label and either an absolute start date, a start day relative to the date of service, or a length of time prior to the date of service. Statements relating to old or previously existing conditions are labeled so as not to be confused with descriptions of the current illness. These are extensions of the time morphing done by the HPI filter and work in conjunction with that morpher (see item 8 above).

13. Temporal: morphs time statements relative to current illness and conditions to a normal form consisting of a modifier (less than, equal, greater than), an integer duration, and a scale (seconds, minutes, hours, days, weeks, months, years).

In the current implementation, morphing is implemented using a "flex" tool, augmented with a push-down stack so as to produce context sensitive grammar. Flex is a finite state automata generator. The addition of a push-down stack transforms it to a context sensitive grammar generator. By integrating the push-down stack directly with the finite state automata, a significant reduction in computing overhead is achieved. It should be appreciated, however, that morphing functionality could be accomplished using a different programming tool, or using a context free grammar generator such as "yacc" or "Yacc++". A context sensitive grammar could also be used.

FIG. 3 illustrates the ordering and overall processes in which the morphers (also known as "lexers") are used in the preferred embodiment. Appendix A is illustrative of the manner in which morphers are built. The example is taken from the temporal morpher. It illustrates the use of a push-down stack, the morphing process, and the formatting of the output.

Parsing

The task of parsing notes is distributed across several processes. Identification and tagging of the grammatical segments of sentences uses the same techniques as are used in the morphers. In the current implementation, there are three separate processes (120) that are used respectively to tag for use with History and Exam, ICD coding, and CPT coding. These are referred to as the H_tagger, the I_tagger, and the C_tagger. The general purpose of these taggers is to:

1. Recognize and discard noise words.
2. Divide and tag at the clause and phrase level based on the rules of punctuation and the use of conjunctions, prepositions, articles, negatives, and relative pronouns.
3. Tag the clauses and/or phrases according to the following semantic categories:

Disposition—how the patient arrived at and left the medical facility.
    Physician involvement—whether an action was taken by the attending physician or a consulting physician.
    Certainty—whether a diagnosis or evaluation expressed by the attending physician is certain or conjectural.
    Negation—identifies negated statements.
    Primacy—whether a diagnosis is primary or is secondary to another diagnosis.
    Quality—whether the clause or phrase is qualitatively modified, and in what way.
    Ordinality—whether the clause or phrase is modified by an ordinal, and of what number.
    Cardinality—whether the clause or phrase is modified by a cardinal, and of what number.
    Topology—whether a clause or phrase is topologically modified, and of what type.
    Imperative—whether the clause is an imperative.

In the current implementation, each clause or phrase is stored in an object that contains data items in which the tags are stored. The same tagging objectives could be obtained using other types of data structures. This parsing method is essentially bottom-up. This is the preferred implementation because physician notes are frequently telegraphic in grammatical style and do not, therefore, easily submit to a top-down parsing method. Top-down parsing, though difficult, is an acceptable alternative approach.

Appendix B contains a portion of the C_tagger showing the clause and phrase objects and a representative sample of the patterns and actions. The preferred parsing and vector processing databases are further described below.

Parsing and Vector Processing Databases

Document parsing and vector processing are both data driven. That is to say, the particular actions taken by the software system is controlled by the content of databases. Accordingly, the data acted on by the parsing and vector processing algorithms may be modified without the need to recompile the software system. This is the preferred method, but coding the control data directly into the software is also possible.

In the current implementation, the only portion of parsing that is data driven is the parsing of entire notes into sections or segments. A note is preferably created in segments each of which has a segment label. There is, however, no standard nomenclature for these labels even though the types of segments that are used are limited. Because each physician may use different labels, it is convenient to maintain these labels in a database.

In the current implementation, this is called the segment table. The segment table is a many-to-one data mapping in which the actual labels that the physicians use are mapped to a single label for each segment type. The segment types used in the current implementation include: chief complaint; allergies; review of systems; physical exam; medications; history of the present illness; past medical history; family and/or social history; course of treatment, critical car; plan; lab data; assessment; disposition; observation. The following sample entry shows the mapping of a number of possible labels for "history of present illness" to the single label "cur_history" which is used internally by the system. Note from this example, that two or more segments are sometimes combined. In this case, the "history of present illness" and "review of systems" can appear as a single segment.

cur_history:
  history |
  identification |
  history of present illness |
  history of presenting illness |
  history of present illness review systems |
  history of present illness review symptoms |
  history of present illness ros
;

The databases used for vector processing fall into two major categories: data that maps directly to medical codes, and data that provides medically relevant knowledge. In the major category of data that maps directly to medical codes, there are two preferable subcategories: International Classification of Diseases, $9^{th}$ Clinical Modification (ICD-9-CM, or just ICD); and Current Procedural Terminology (CPT). There are, however, other less popular medical coding sets that could be used instead.

In the current implementation, the codes for diagnoses are taken from ICD database 140 and the codes for medical services, including interpretation of test results, procedures, and level of medical service provided, are taken from CPT database 145. (While ICD codes are in the public domain and may be freely used and distributed, CPT codes are the property of the American Medical Association).

The ICD databases 40 consists of many-to-one relations between the text vectors that represent possible ways to state a diagnosis and the numerical code for that diagnosis. Because the number of vectors required to obtain good coverage is high (currently well over one million), and because the vectors for a particular ICD code may vary only slightly from, each other, the current implementation permits the vectors to be written as cross-products of subvectors. This is a convenience for the sake of implementation and maintenance ease and reduction of storage space. It is, however, entirely feasible to store each vector in full form.

An exemplary description of the syntax and semantics of the ICD database 140 are shown below.

| Syntax Description (in BNF notation) | |
|---|---|
| table | := code_descriptions |
| | \| rewrite_rules |
| | \| comments |
| code_descriptions | := code_descriptions code_description |
| | \| code_description |
| code_description | := code vectors ";" |
| | \| code ";" |
| | (NOTE: some codes do not have vectors since the vectors may not yet be defined or if the code is assigned based on a combination of other codes. Codes that are truly the latter should be completely commented out.) |
| code | := [0-9] [0-9] [0-9]? [0-9] ? [0-9] ? |
| vectors | := vectors vector |
| vector | := text "\|" |
| | \| text |
| | \| "{" vector "}" |
| text | := words |
| | \| "NULL" |
| | \| "NOS" |
| | \| "NEC" |
| | \| rewrite |
| words | := words word |
| | \| word |
| rewrite_rules | := rewrite_rules rewrite_rule |
| | \| rewrite_rule |
| rewrite_rule | := "<<" rewrite_name "=" vectors ">>" |
| rewrite_name | := [0-9a-zA-Z ]+ |
| | (NOTE: the blanks in a rewrite_name should be ignored) |
| rewrite | := "<" rewrite_name ">" |
| comments | := comments comment |
| | \| comment |
| comment | := /* text */ |
| | \| // text EOL |
| ignore terms | unspecified |
| | other |
| | by |
| | for |
| | with |
| | due |
| | to |
| | , |
| | . |
| | : |
| | NOS and NEC if not alone on a line (see the notes on semantics) |

Semantics Description

Each code has one or more associated vectors. Vectors can be delimited by the '|' character. Example:

```
111.11                a b c |
                      a b d
;
``` where there are two vectors (a b c) and (a b d).

A set of vectors can be specified using brackets to produce a cross-product as in:

{a (b | c)} which should be expanded to vectors:
(a b)
(a c)

or:

```
{a |
  b {c |
      d}}
``` which should be expanded to:
(a c)
(a d)
(b c)
(b d)

The rule is that each nested set is crossed with each previous element. Nesting can be unlimited, hence:

```
{a |
  b {c |
      d {e}}}
``` expands to:
(a c e)
(a d e)
(b c e)
(b d e)

The appearance of "NULL" "NOS" "NEC" alone as an element indicates that there is a null element in the bracketed set, hence:

```
{a |
  b {NULL
      c |
      d {e}}}
``` expands to:
(a e)
(a c e)
(a d e)
(b e)
(b c e)
(b d e)

The terms "NOS" and "NEC" should be ignored when occurring with other words as in "warts, NOS". The reasons for maintaining a distinction between NOS/NEC and NULL are that NOS/NEC are used in ICD-9-CM. NULL is introduced by the author as needed. Ignore terms are included for readability in some cases. They are not be included in vectors. Words appearing multiple times in a vector description are only entered once in the final vector.

The following is an example of several ICD database entries for diabetes.

```
<< 250.0 = { Diabetes |
    diabetic {
        NULL |
        brittle |
        congenital |
        familial |
        mellitus NOS |
        severe |
        slight |
        without complication }} >>
<< type I = type I |
    insulin dependent type |
    insulin dependent |
    insulin-dependent |
    IDDM |
    juvenile type >>
<< type II = type II |
    non-insulin dependent type |
    non-insulin dependent |
    non-insulin-dependent |
    noninsulin-dependent |
    NIDDM type |
    adult-onset type >>
    250.00   { <250.0> { NULL | <type II> }};
    250.01   { <250.0> { <type I> }};
    250.02   { uncontrolled { <250.0> { NULL | <type II> }}};
    250.03   { uncontrolled { <250.0> { <type I> }}};
```

Figure 4:
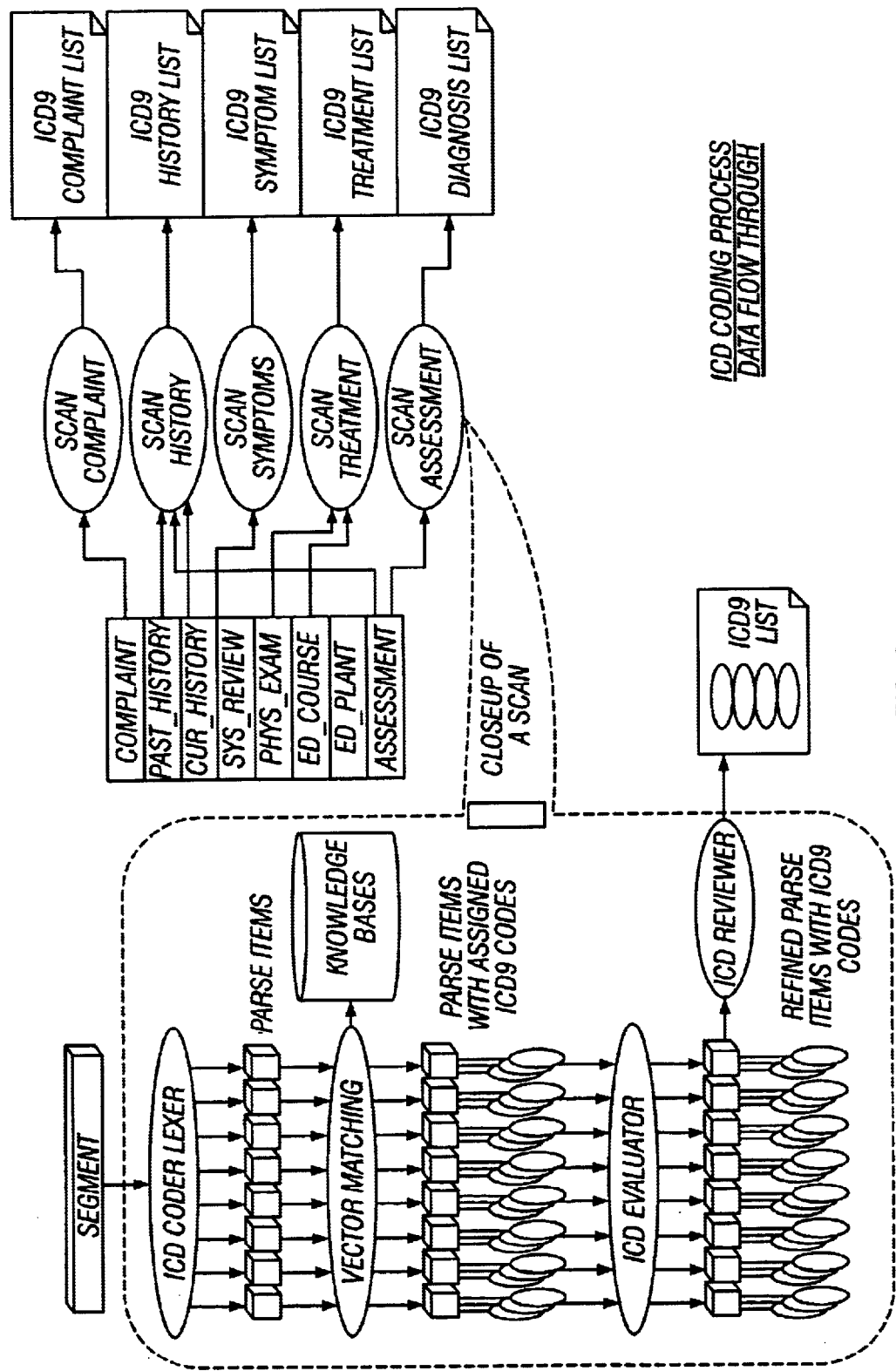
FIG. 4 is shows the flow through the preferred ICD coding process.

FIG. 4 shows the flow through of an ICD coding process. Of the approximately 15,000 ICD-9-CM numerical codes, an exemplary implementation might use approximately only 3000. It has been determined that only about 100 codes account for 80% of the diagnoses assigned at many medical facilities. To account for the approximately 12,000 ICD codes that may not be covered in the ICD database 140, the ICD database 140 is supplemented with a semi-knowledge ICD database.

In the preferred embodiment, vector comparisons between parse items and vectors in the semi-knowledge ICD database 140 are performed under the control of second vector matching module 64—see FIG. 1. The semi-knowledge ICD database 140 is composed of vectors that describe broad classes of diagnoses along with a listing of the specific codes that are related to each broad diagnosis class. If the system identifies a broad diagnosis class from the semi-knowledge ICD database but fails to identify at least one of the specific ICD codes that occur in the associated code list, then the location of the broad diagnosis indicator in the note is stored, and the note is submitted, with that location high-lighted, for human review. The following example shows an entry in the semi-knowledge database:

SK10042 {Acanthosis} [701.2 701.2 757.39 757.39 530.89 701.2 529.8]

Weighting is a basic feature of text vectors. Rather than maintain the weighting factors in the same location as the text, the current implementation uses separate database entries that map the weights to the text in the ICD database. It is entirely feasible to maintain the weights with the text, but this can be cumbersome and difficult to maintain. In the current implementation text items can have one of three weights, but any number of weighting factors can be used. The text items with the highest weighting factor and lowest weighting factor are listed as separate data columns. All text items not appearing in either of these data columns are given the middle weighting factor. In the preferred embodiment, the actual weighting factors are not stored in the database, but are set in a system configuration file.

The CPT database 145 contains vectors for procedure and interpretation codes. The syntax and semantics are similar to the ICD database with one important extension. The vectors associated with each numerical code are subdivided into those that are mandatory and those that are optional. This is in place of weighting of individual terms. The reason for the difference is that the descriptions of procedures and interpretations are often longer than the descriptions of diagnoses. That is to say, the description of a procedure or interpretation often consist of several sub-descriptions spread over several sentences. The sub-vectors in the CPT database correspond to the various sub-descriptions that a physician would note in the description of a procedure or interpretation. The following example is for surgical or diagnostic endoscopy with dilation.

```
46604 {
    procedure.1    { < anoscopy > | < endoscopy >}
    procedure.2    { < dilation > }
    location.1     { anus }
};
```

The CPT database 145 has vectors for about 1500 procedure and interpretation codes. Approximately less than 50 codes account for about 80% of the interpretations and procedures performed at any particular medical facility. Semi-knowledge for CPT codes works in the same manner as for ICD codes.

CPT level of service codes (Evaluation and Management, or EM codes) are based on a combination of many factors. These factors are documented in the CPT manual and in numerous publications from the Health Care Finance Administration and other private publishers. In summary, the factors are:

1. Chief complaint
2. History of present illness
   Location
   Quality
   Severity
   Timing
   Context
   Modifying factors
   Associated signs and symptoms
3. Family medical history
4. Past medical history
5. Social history
6. Review of systems:
   Constitutional
   Eyes
   Ears, nose, mouth and throat
   Cardiovascular
   Respiratory
   Gastrointestinal
   Genitourinary
   Musculoskeletal
   Integumentary
   Neurological
   Psychiatric
   Endocrine
   Hematologic/Lymphatic
   Allergic/Immunologic
7. Physical examination of:
   Eyes
   Ears, nose, mouth and throat
   Cardiovascular
   Respiratory
   Gastrointestinal Genitourinary
Musculoskeletal
Skin
Neurologic
Psychiatric
Hematologic/Lymphatic/Immunologic 8. Data reviewed—lab and diagnostic tests, old records, consultations with other health professionals.
9. Differential diagnoses and management options.
10. Risk based on the medical condition of the patient and the management options chosen by the physician.
11. The level of medical decision making required by the patient's condition.

In the current implementation, there are vector databases 135 corresponding to each of these factors. These databases have a format similar to the ICD database 140.

Level of service coding is based on the complexity of medical decision making. The complexity of medical decision making is determined from: the actual and possible diagnoses considered by the physician along with the possible management options; the amount and complexity of medical records, diagnostic tests, and/or other information that must be obtained, reviewed, and analyzed; the risk of significant complications, morbidity, and/or mortality, as well as co-morbidities, associated with the patient's presenting problem(s), the diagnostic procedure(s) and/or the possible management options. Vector databases are defined to cover the second area of review and consultation. These are in the same format as the ICD database. The first and third areas relating to diagnoses and risk are handled using two databases that tie diagnoses and management options to risk. The first of these databases consists of couplets that associate particular diagnoses with one of five base levels of risk associated with each diagnosis. The second database defines management options, the degree to which they increase the complexity of medical decision making, and the diagnoses in conjunction with which they increase complexity.

Finally, with regard to the databases, there are several databases that codify certain medical knowledge. These three databases include anatomy, drugs, and microbiology databases, 150, 155, 160, respectively.

The anatomy database 150 provides synonymy and part-whole relations and is secondary to the ICD and CPT databases 140, 145. Anatomy database 150 is used to determine codes that are sensitive to the body part being affected. The ICD and CPT databases do not contain all the possible synonyms for the names of body parts nor do they list all the subparts of each body part. The anatomy database might for example include a hierarchical listing of the body's parts by body system. The following example is an excerpt from the database showing a partial set of part-whole relations involving the skeletal system and the femur:

Bone: Femur: head of femur
;
Bone: Femur: upper epiphysis of femur
;
Bone: Femur: neck of femur
;
Bone: Femur: base of neck of femur
;
Bone: Femur: intracapsular section of femur
;
Bone: Femur: midcervical section of femur
;
Bone: Femur: cervicotrochanteric section of femur
;

The anatomy by region database defines the anatomical part-whole relations based on body region rather than body system. The following example is a partial section from the trunk region:

Trunk: thorax: breast
;
Trunk: thorax: breast: nipple
;
Trunk: thorax: breast: areola
;
Trunk: thorax: posterior chest wall
;
Trunk: thorax: posterior chest wall: latissimus dorsi muscle
;
Trunk: thorax: posterior chest wall: rhomboideus major muscle
;
Trunk: thorax: posterior chest wall: rhomboideus minor muscle
Trunk: thorax: posterior chest wall: rhomboid
;
Trunk: thorax: posterior chest wall: levator scapulae muscle
;
Trunk: thorax: posterior chest wall: serratus posterior muscle
;
Trunk: thorax: posterior chest wall: erector spinae muscle
;

The anatomy database may further define synonyms in the same format used in the ICD and CPT database definitions. The following is an excerpt for the gluteal region. Although the format is like that of the rewrites in the ICD and CPT database definitions, the effect is that the terms listed here are interchangeable as synonyms:

<< gluteal region=buttock |
  gluteus |
  gluteal |
  sacroiliac region >>

The drug database 155 defines the hierarchical relation of drugs. The basic categories are illegal drugs, low maintenance prescription drugs, high maintenance prescription drugs, over-the-counter drugs, and poisons. The subcategories are those defined in ICD as specific to the correct coding of various chemical related diagnoses. The following is an excerpt from the poisons database:

Poison: Methyl Alcohol: Alcohol radiator
;
Poison: Methyl Alcohol: Alcohol wood
;
Poison: Methyl Alcohol: Antifreeze alcohol
;
Poison: Methyl Alcohol: Canned heat
;
Poison: Methyl Alcohol: Carbinol
;
Poison: Methyl Alcohol: Methanol
;

Poison: Methyl Alcohol: Methyl alcohol
;
Poison: Methyl Alcohol: Methyl carbinol
;
Poison: Methyl Alcohol: Radiator alcohol
;
Poison: Methyl Alcohol: Wood alcohol
;
Poison: Methyl Alcohol: Wood spirit
;

The microbiology database 160 defines the synonyms and hierarchy of viruses, bacteria, and parasites that are associated with ICD diagnoses as in the following example:

Bacteria: *Clostridium: Clostridium tetani*
;
Bacteria: *Clostridium: Clostridium botulinum*
;
Bacteria: *Clostridium: Clostridium perfringens*
;
Bacteria: *Clostridium: Clostridium difficile*
;

Further, the microbiology database defines the diseases that are related to various microorganisms as in the following example:

Bacterial disease: gas gangrene: *Clostridium: Clostridium perfringens*
;
Bacterial disease: food poisoning: *Clostridium: Clostridium perfringens*
;
Bacterial disease: Colitis: *Clostridium: Clostridium difficile*
;

Referring back to the discussion on parsing, parsing is used to identify sentences and to break them into component phrases and clauses. The parse granularity is different depending on the section of the document and the type of codes that are being processed (diagnosis, procedure, or EM level). The components produced by the parsing process are called parse items. Because the granularity differs among the three types of codes processed, the document sections are copied onto three separate lists. This allows different parsing granularity to operate on the same section of text.

The granularity of the parse for the three types of codes is influenced by two factors: (1) the granularity of the knowledge bases which define the codes, and (2) the specific techniques used in the vector processing to associate parse items with specific codes. Both of these factors are driven by the nature of the codes being assigned. Diagnosis coding requires fine granularity to distinguish the precise medical condition along with related factors such as body location or parts, micro-organism involvement, or drug involvement. Most ICD9 diagnoses represent single concepts and can be expressed in one sentence or in part of one sentence. The ICD9 knowledge base used in the current implementation reflects this structure with the majority of vectors being less than five words. Fine grained parsing produces parse items which can be directly compared, using vector processing, with the ICD9 knowledge base.

Fine grained parsing breaks text at most prepositions, verbs, conjunctions, and punctuation dividing clauses. Parsing done as described herein does not require grammatical correctness, at either the fine-grained level used in diagnosis coding or the coarser level used in procedure and EM level coding. The words or punctuation that break the text form the boundaries of parse items. The words lying between the two consecutive boundaries are treated as a single parse item. The boundary terms or punctuation are assigned tags corresponding to a predefined organization of grammatical links. These grammatical links define simple semantic relations between the concepts represented by the parse items. For diagnosis coding, these links are important in establishing compatibility and reasonableness tests for combining parse items as well as setting the scope for combinations and comparison.

In addition to the grammatical links which divide parse items, parsers recognize and categorize conceptual modifiers such as "negation", "history", "possible", "probably", "rule-out", and "versus". Modifiers such as these are expressions in standard usage which have a particular meaning in the context of outpatient medical coding. For each of the expressions listed above, an associated diagnosis statement would not be coded. These modifiers are stored as data elements attached to parse items. A second class of conceptual modifiers are statements of quantification, time, extent, and duration previously identified by the morphological processing. Statements such as these provide important information in calculating specific diagnosis codes.

Parsing for procedure and EM level coding is coarse-grained with parse items broken at conjunctions and punctuation dividing sentences. This reflects the scope needed to recognize the concepts represented in procedure and EM level coding. Procedures typically require one or more sentences to fully describe activities performed by the medical professional. EM level coding requires an identification and accumulation of specific points of the history, physical examination, and diagnostic testing and assessment documented by the medical professional during the encounter. Identifying these items requires a thorough reading of the full document. Coarse grained parsing allows these points to be matched in their sentential context. A coarse-grained approach does not work for diagnosis coding because of the level of precision necessary. As noted above, there are approximately 15,000 ICD9 codes. The categorization required for EM level coding is roughly two orders of magnitude less.

Parsing for procedure coding recognizes statements describing the context of the activity. This includes procedures performed by medical professionals other than the physician who is billing for the encounter, such as physician assistants, medical residents, paramedics, or nurses. The location where the procedure was performed, whether in the field or in the hospital is also recognized by the parser. A third type of context is the timing of procedures. More specifically, the parser looks whether a procedure has been performed or whether it is "planned" for the future. Procedures described as planned in the note cannot be coded.

Vector Processing

Figure 5A:
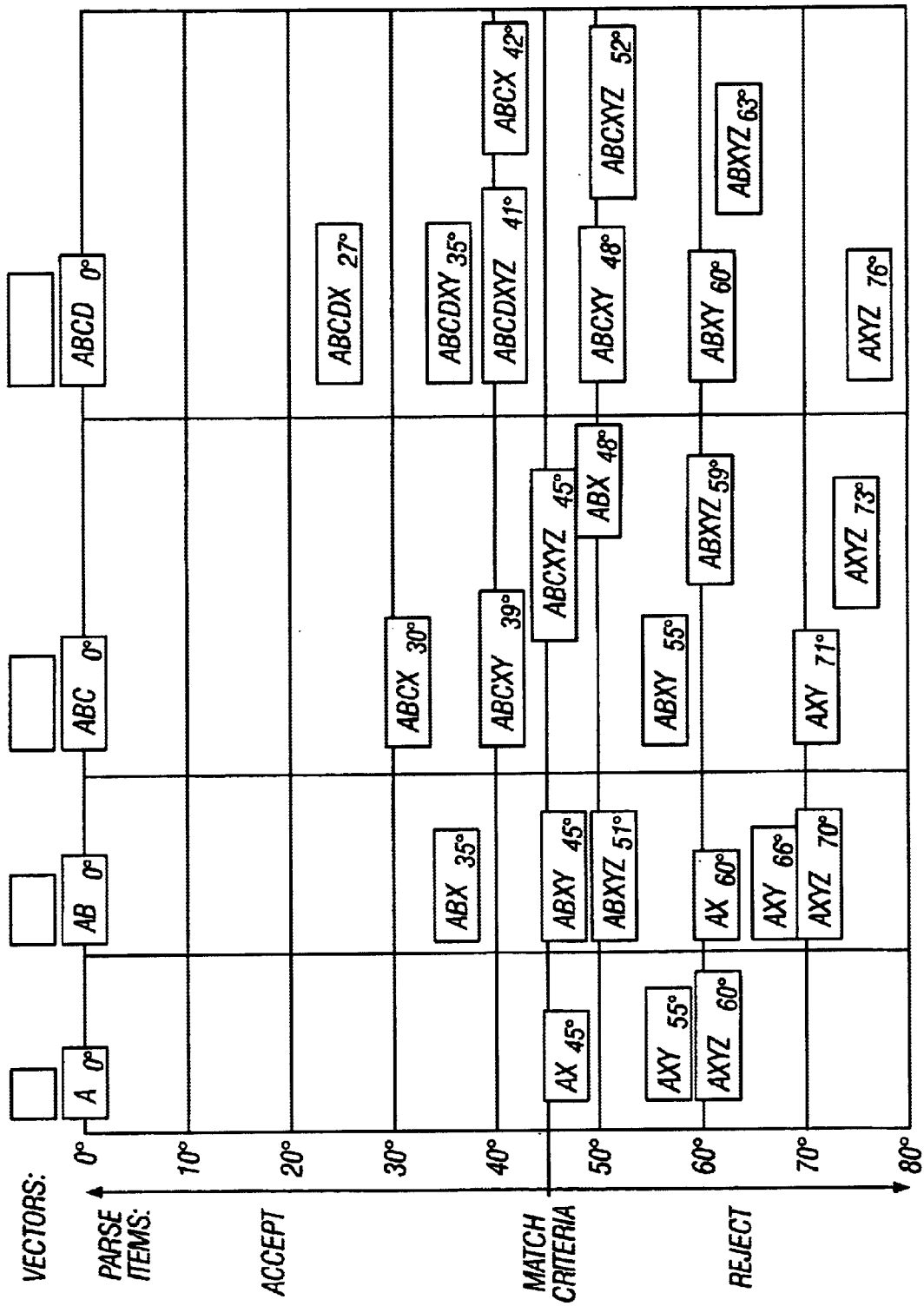

Vector processing flow through is illustrated in FIGS. 5(*a*)–5(*e*). Vector processing is used to associate parse items with specific diagnoses, procedures, or EM level codes. In the current implementation, a vector defines a set of words. The databases are organized by grouping together a set of vectors under a common descriptor. Typically this descriptor is a code number representing a diagnosis, procedure, or a component of the EM level. Code numbers are assigned to individual parse items by comparing the vectors defined in the database with the set of words in a parse item and measuring the difference. The code number with the smallest difference and below a maximum threshold is assigned to the parse item. The maximum threshold for a match is a configurable parameter. This basic strategy is used for fine-grained parse items for the initial assignment of diagnosis codes. Assignment of procedure and EM level codes uses a similar strategy adjusted to account for coarser granularity of the parse items.

Vector difference is quantified by measuring the angle between two vectors. The smaller the angle, the more words in common between the two vectors. Orthogonal vectors share no common words. The angle ($\theta$) between two vectors may be calculated using the formula shown below. The subscripts in this equation denote different dimensions. In this calculation, each unique word in a vector is a different dimension. The vectors X and Y shown below have two common dimensions, hence two common words. The order of the words in a parse item or vector definition has no effect on the vector difference calculation.

Vector X: $x_1, x_2$

Vector Y: $y_1, y_2, y_3$ $\theta = \cos^{-1}((x_1y_1 + x_2y_2)/(\sqrt{x_1^2 + x_2^2}\sqrt{y_1^2 + y_2^2 + y_3^2}))$ To efficiently compute the large number of vector calculations necessary in this system/method, a dynamic programming algorithm is used. This algorithm stores each possible vector match as a bit array with the bit arrays associated with one parse item stored in a list sorted by code number. Because each component of the vectors is unit sized, the vector difference calculation can be simplified to the formula shown below:

$\theta = \cos^{-1}((\text{\# of common dimensions})/(\sqrt{\text{\# of X dimensions}} \sqrt{\text{\# of Y dimensions}}))$ The dynamic programming algorithm used here along with the simplified formula offers significant performance advantages over an iterative approach using the standard formula (more that a 10× improvement in processing speed). Both approaches require an inverted index that maps each word to a list of vectors that contain the word. The inverted index can be implemented as a sorted vector, B-tree, or hash table. However, the simplified formula requires that only the number of words in each vector be known in order to complete the vector difference calculation. This reduces the storage requirement for the vector index to simply an array of positive integers. The standard approach requires a full vector index with the individual terms stored for each vector.

Several improvements account for the efficiency and precision of the new dynamic programming algorithm. First is the use of libraries of high and low weight terms. A high weight term is a word that, if present in a vector definition, must be present in the parse item to get a match. A low weight term is a word that, if is present in a parse item, will reduce by one the number of dimensions from the parse item. For diagnosis coding, high weight terms include primary medical conditions and body parts. Low weight terms include adjectives denoting severity and quality as well as topological words. In the dynamic programming algorithm, the high and low weight terms for each possible vector match are stored as second and third bit arrays attached to the primary bit array. Another technique to improve efficiency is the use of heuristics when selecting vectors to compare against a parse item. In order for two vectors to have a small difference, the number of words in each, excluding the number of low weight terms in the parse item, must be relatively close. Vectors with a length much greater or much less than the number of terms in a parse item do not need to be considered when computing vector differences. A length heuristic filters out vectors that have no possibility of matching.

Vector processing for procedure codes has several important extensions to the basic technique described above. By nature, procedures in general require longer explanations than diagnoses. A procedure description can include naming of the medical treatment, listing materials or instruments used, and naming of the body location or system involved. Each of these items can be a discriminator in selecting the correct CPT code.

To cover a larger context, a two-stage approach is used to match procedure codes. In the first stage, the essential elements of procedure codes are identified and classified. These include descriptions of medical treatments, materials, instruments, body locations, and body systems. The second stage takes the elements identified and compares them against procedure definitions. Both stages use a vector difference computation with an enhanced version of the dynamic programming algorithm.

The enhanced dynamic programming algorithm used for procedure coding accommodates multiple parse items, rather than just one, when computing vector differences. This allows matching of vectors across a larger scope. The size of this scope, or window, is a configurable parameter set individually for stages one and two: The stage one window is small because individual elements of procedures can be described in one or two parse items. The stage two window is larger in order to cover complete descriptions of procedures.

Parse items are processed one section at a time from top to bottom, so as a section is processed, the windows slide through the text, at each point defining the extent of the vector difference calculation. The stream of code numbers matched in stage one represents the elements of procedures and is used as the input to stage two. Similar to the vector processing for diagnosis codes, high and low weight terms are used to improve efficiency and precision.

Because of the coarse granularity of parsing done for procedure-coding, a modified form of the vector difference formula is used. In this form, the number of dimensions, or words, in all of parse items covering the current scope is not factored into the calculation. Instead, the difference is based upon the number of common terms and the number of terms in the possible matching vector. This implicitly treats words in the current scope which are not part of the possible matching vector as low weight terms. Accordingly, the modified vector difference formula is:

$\theta = \cos^{-1}((\text{\# of common dimensions})/(\text{\# of X dimensions}))$ An important aspect to the correct coding of procedures is the interpretation of numerical expressions in the note. During parsing, these statements are treated as conceptual modifiers and are stored with the closest parse item. These expressions can describe the size of a wound or lesion, the amount of time taken for a particular medical treatment, or the number of repetitions of a treatment. Each of these items is a potential discriminator for selecting the correct procedure code.

The current implementation uses an interval index to map numerical expression to their correct interpretation. An interval index for numbers is similar to an inverted index for words. An interval index, when given a numerical value, returns a list of predefined numeric ranges within which the number falls. These ranges are part of the vector definition of certain procedure codes. The interval index works by storing a sorted array of discreet points with each point containing a list of ranges that it is a part of. Looking up a number in the interval index is matter of finding the point with closet numeric value and returning its associated list.

Vector processing for EM level codes is similar to the processing done for diagnosis codes. One parse item at a time is used to compute the vector difference. Similar to procedure coding, the modified vector difference computation is used which does not factor in the number of words in a parse item. EM level codes are determined by accumulating individual elements of history, physical examination, diagnostic testing, and the final assessment. The individual elements are matched during vectors processing and stored in a list to be tabulated in code resolution.

Code Resolution

The code resolution algorithm 130 is a knowledge base tool that combines, adds and/or removes specific codes based on "concept refinement" and industry coding standards. Concept refinement is interleaved with the vector processing and is driven by the goal of reaching minimum vector difference. The process for enforcing coding standards accepts the codes output from vector processing and applies the rules defined in ICD9 and CPT related to specific, co-occurrence, and ordering. Also part of code resolution is identification of physician notes that require further review. All of these processes are driven by a set of knowledge bases 165 that embody both published regulations as well as medical coding expertise elicited from industry experts.

Concept refinement is a technique for modifying and combining parse items in grammatically and semantically valid ways. This technique is used for diagnosis coding in order to broaden the context of fine-grained parse items. After the initial code assignment is made by vector processing, the parse items and the intervening grammatical links are analyzed to detect related concepts. Certain classes of grammatical links, such as conjunctions or prepositions, indicate related concepts that may represent a single diagnosis code. To verify this, two adjoining parse items separated by these particular classes of grammatical links are combined into a new parse item. This new parse item is resubmitted to vector processing to compute a vector difference. If this vector difference is smaller than either of the two component parse items, then this new combined parse item replaces the two smaller ones.

In addition to combining adjoining parse items, more complex combinations are tested for expressions that list multiple body locations for a condition or multiple conditions for one body location. A second aspect to code refinement is the use of body part, drug, and microorganism hierarchies in order to generalize expressions in the physician note that may be too specific to map directly to a diagnosis code. Parse items that are not assigned diagnosis codes are scanned for words that fall in the body part, drug, or microorganism hierarchy. Words that match are replaced by a more general expression and the modified parse item is resubmitted to vector processing.

Processing for industry coding standards enforces the published coding regulations to produce a finished set of diagnosis, procedure and EM level codes. The rules applied here enforce constraints of code co-occurrence, specificity, and ordering. Individual ICD9 codes have constraints that include or exclude certain other ICD9 codes. This process has rules that detect and fix situations that violate these constraints.

A second aspect of co-occurrence is the linkage ICD9 and CPT codes. Diagnosis codes need to be linked to a procedure or EM level in order to justify the procedure or EM level code. A cross-coding knowledge base containing a library of acceptable linkages is used to verify the procedure codes as well as assign the correct linkages. Medical coding requires that diagnoses and procedures be reported to the greatest level of specificity possible. To support this, ICD9 and CPT hierarchies are used to help decide which codes are more specific than others. Likewise, ordering of diagnosis codes is important to indicate which conditions are most serious.

The medical coding process uses a knowledge base of ICD9 codes with associated priority assignments to help decide how diagnosis codes should be ordered. CPT and EM level codes are ordered by level of reimbursement. The highest reimbursing codes are listed first. As all of these functions that apply industry-coding standards are executed, a series of tests are run which decide if the codes assigned to the physician note require further review. These tests measure the ambiguity of the documentation by comparing the signs and symptoms with the final diagnosis, assessing the level specificity for diagnosis and procedure codes, and detecting situations, such as involvement of physician assistants or medical residents, that may require independent confirmation.

A capability of the medical coding process is the association of diagnosis, procedure, and EM level codes with the portions of the note that support the code assignment. This "trace" capability provides verification and explanation of the internal algorithms. To compute the trace, the extents of the parse items matching each code must be mapped back to the correct character offsets in the original document. Morphological processing alters the original stream of characters to facilitate parsing and vector processing. To recover the character offsets in the original document, an edit array is computed which stores a byte offset for each character in the morphed stream from it position in the original document. A conventional file comparison algorithm is used to compute the minimum edit distance from the morphed form to the original form. The edit array is calculated from the edit distance by enumerating the edit distance for every byte offset of the morphed document.

Coder Review Workstation

The coder review workstations (CRW) 85, 99, which may reside at the host site 20 or the client site 30, are available to perform a number of different functions. These include (1) providing provider and payer specific code resolution, (2) displaying coding results for quality assurance reviews, and (3) formatting output for paper or electronic claims submission. A CRW can also be used as a data communications link between the data center and the client site.

Although the vast majority of the system described above is coded in C++, in the preferred embodiment, the CRW code has a much different set of requirements from the majority of the data center and medical coding processes. The CRW code carefully separates the actual graphical user interface (GUI) layer from business rules and logic. In the preferred embodiment, the GUI is written in Visual Basic (but has also been prototyped in JavaScript and Microsoft Access).

Conventional Component Object (COM) modules may be used as the interface between the CRW and the classes/objects used by the bulk of the data center system code. Business rules and logic are incorporated into COM objects. The COM objects in effect represent the middle tier in a three-tiered architecture: human interface-business rules-data repository.

As the CRW code has a much different set of requirements from the majority of the design represented within this document, the design of the COM wrappers deviates, in many cases, from that of the underlying C++ classes that might be in use. In many cases, the COM wrappers will incorporate more than one C++ class.

Figure 6:
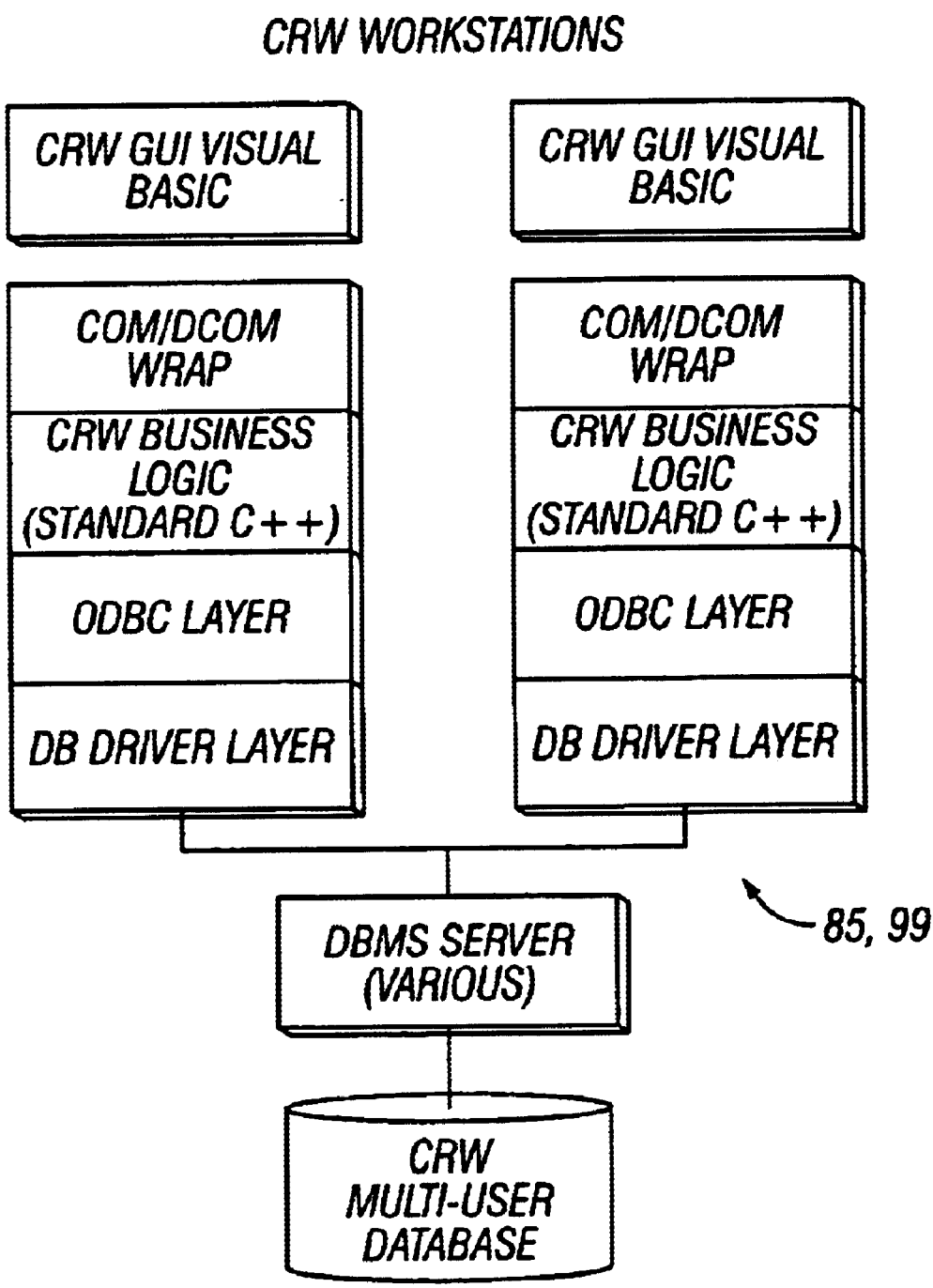
FIG. 6 is an architecture diagram of a coder review workstation.

FIG. 6 is a block diagrammatic illustration of a coder review workstation 85, 99 (from a functional perspective)

showing the provider and payer specific components of the resolver, and output processing for the interactive graphical user interface, paper form printing, and electronic output.

The following sections briefly describe the associated CRW objects for:

Performing data lookup.

Managing the quality assurance work queues.

Managing data communications.

Performing the actions associated with the GUI.

CRW Data Lookup—Performing Data Lookup

This object provides the lookup facilities in the CRW. The interface to the CRW code is implemented in the form of an OLE custom control.

The CCDCPTLookup OCX Control provides the CRW code with a lookup mechanism for the ICD/CPT data. This component uses the CDBLookup class to implement the database specific search functionality. This control has exemplary interface properties and methods shown in Appendix C.

VB Modules and Design—Performing the Actions Associated with the GUI

The table in Appendix D lists the GUI events and actions. These are representative of the current implementation, but some events and/or actions could be deleted or others added within the intended scope of the system.

Differences Between Data Center and Client CRW Versions

There are several differences in functionality between a host CRW 85 and a client CRW 99 at a customer site. A configuration option is set to indicate the version for each CRW workstation. The different behavior is implemented within code logic so that there is only one version of code to maintain.

The differences between the versions are as follows:

Client-CRW does not show EM components—implement this as a configuration file switch.

Graphics for 'Check Inbox' & 'Send to Billing' are different.

Customers only get 4 ICD codes; local has up to 9.

Active Coder

Figure 7:
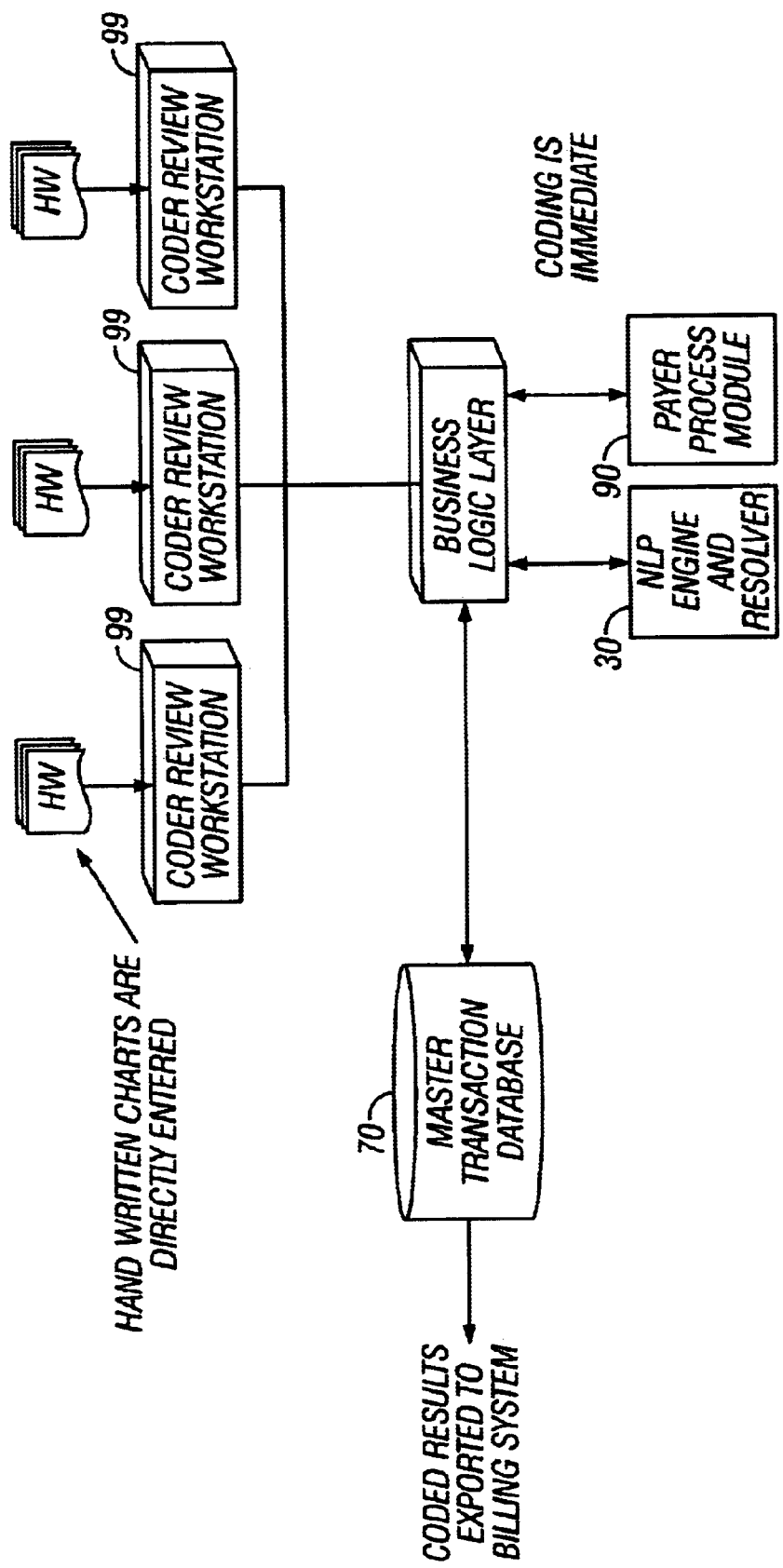
FIG. 7 shows an Active Coder implementation.

Many physician notes are hand written and are therefore not directly accessible to the NLP engine. FIG. 7 shows an Active Coder solution that is a variant on the Coder Review Workstation implementation described above. The Active Coder solution provides a graphical user interface that enables a clerical worker to enter information from the physician note directly into the language processing engine and resolver using keyboard or automatic speech recognition. The physician note is thus codable in real-time. This system is a substantial advance in the state-of-the-art over all other available "coding tools" in that it incorporates both the ability to find the correct codes based on the input but also has the ability to reason from the codes and other information to determine associated codes.

Unlike conventional "coding tools", the user does not need to understand the rules and guidelines of medical coding in order to produce a fully coded medical bill.

Physician Coder

Figure 8:
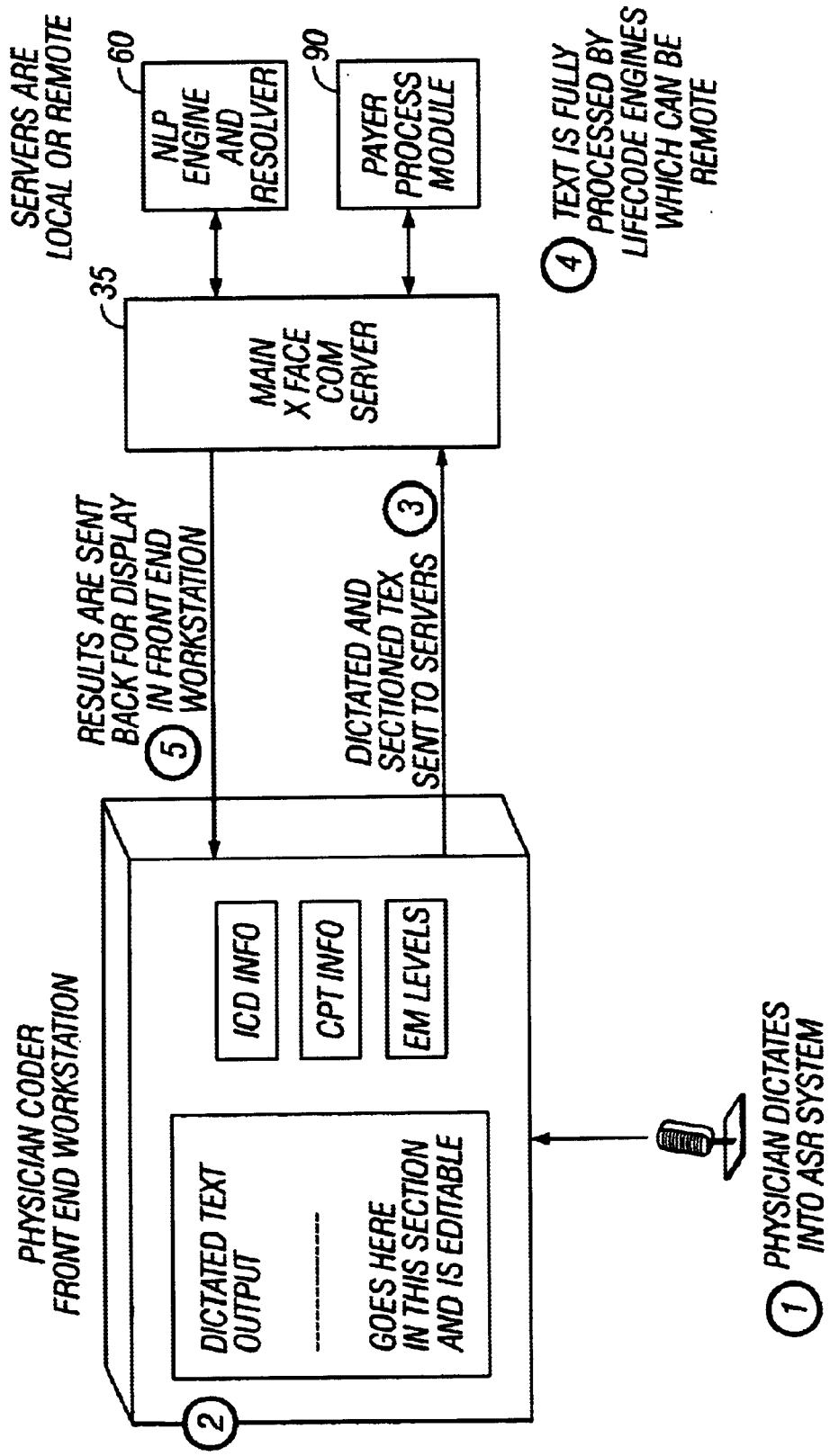
FIG. 8 shows a Physician Coder implementation.

FIG. 8 shows a Physician Coder solution that is yet a further variant on the Coder Review Workstation implementation. Using keyboard or automated speech recognition, a Physician Coder front end workstation interacts with the physician to produce both the note and the clinical and billing codes in a single interactive session. The workstation uses a set of template note modules from which the physician may pick and choose. Each template is complete in itself, however, each has a set of predefined sections that can be sequentially highlighted and changed in order to document the specifics of the current case that may vary from the template. Also, any portion of the text can be selected and changed using the keyboard, mouse or speech commands. By using a custom (modular) template approach rather than a complete template approach, the workstation efficiency could drastically improve a billing department's caseload.

Software Implementation Details

The basic executables of the illustrated embodiment are written as 32 bit C++ executables. These executables are controller by the Master Process Module 75 at the host site 20. The executables typically poll for work to do, either searching a subdirectory landing zone, listening on a network socket or COM/DCOM connection, or polling the various databases in the Master Transaction Database 70. Alternately, this function can be done using an MS Transaction Server and Message Queuing, or a Conventional Common Object Request Broker Architecture (CORBA). This allows further centralization of the control of the executables, the communication between them and the dynamic instantiation of additional executable threads.

The CRW code is a Visual Basic GUI with a set of C++ objects at the business layer, wrapped in a COM layer. All of the executables use Open Data Base Connectivity (ODBC) or Remote Data Object (RDO) technology for connectivity to the various databases. Each executable file has a configuration file (*.cfg) where various parameters are stored, such as subdirectories to poll against, polling rates, and database to connect.

Multiple instantiations of each of the executables may be launched concurrently to run alongside each other by performing typical lock checks so as not to collide on an individual file or database record.

Processing Status, Category and Rules Flags

The processing of the note and DocumentMaster object (described below) requires it moving through several steps, including being processed by each of the server modules. In addition, there are various categories of the note itself, mostly set by various filters and the medical coding process itself. These categories are indicated by a status field and are used by the host site 20 to determine when a note is ready for the next processing step.

STATUS FIELD: The status field exists in the DocumentMaster table. Each time it is updated, the old status is saved in a row in the StatusHistory table, including the server process and datetime of the update. The status field currently indicates the following states:

1. Imported
2. Converted
3. Rectified
4. Input to NLP engine
5. Received from medical coding process—Needs QA Review
6. Received from medical coding process—No QA Review Needed
7. Reviewed by QA—Completed, Pending Rules
8. Reviewed by QA—Completed with Rules
9. Reviewed by QA—Still Incomplete 10. Ready for Client—Pending Rules 11. Ready for Client—Rules Completed The medical coding process sets the DocReview flag, which drives the status to Needs Manual Review or not. This flag is used by the CRW queues to quickly determine which records need quality assurance review.

CATEGORY FIELD: This field is first set by the Filter mechanism and refers to the transcription state itself. It may have the following values:

1. Complete
2. Addendum
3. Incomplete
4. Incomplete pending addendum
5. Incomplete section headings
6. Incomplete demographic information
7. Intentional blank words (incomplete)
8. Unrecognized file format BILLING REVIEW FLAG: This is a standard Boolean flag indicating whether the Rule Processing has occurred or not. Once Rule Processing has occurred, the Rule Server sets the status flag to "ready for client", assuming it does not need quality assurance review. The possible values are:

0. Rules Not Processed
1. Rules Completed

Entity Relationships and Database Descriptions

MASTER TRANSACTION DATABASE 70: Houses all of the documents (physician notes) and their entire status history including medical coding process output and all processing milestones. Records are frequently purged from this production database for performance reasons. Processes read and write to this database as they perform transformation operations against the document master records. Additionally, some triggering of processing occurs based on a status update to a record in the database.

ARCHIVED DATABASES: Comprises date and client driven snapshot of the documents and processed data that occurred during that time period and for N number of clients. This permits retrieval of processed notes along with the medical coding process version in place at that time in order to reproduce the outcomes at any later date.

METADATA CONVERSION DATABASE: Contains client-specific data that refers to the special processing needs. This includes data to describe the file directory landing zones and input channels from certain clients, information on the header information to be encountered, conversion formats, and lexical preprocessor to utilize.

MEDICAL CODING PROCESS DATABASES: The data that drives the medical coding process. There are 4 main areas of data in the Master Transaction Database 70:

1. The DocumentMasterTable and its supporting child tables consist of the DocumentMasterTable, and the child tables DocumentECodesTable, DocumentCPTsTable, DocumentICDsTables, DocumentHilitesTable and the status table entitled DocumentStatusHistoryTable. There is a one-to-N relationship between the DocurmentMasterTable and all of these.
2. The LookupTables are read-only tables and are used by the CRW code. The medical coding process produces values whose corresponding descriptions are stored in these tables. These are only used for display purposes.
3. The BillingCompanyTable and its children consist of the BillingCompanyMasterTable, along with its children, the BillingCompanyPayablesTable, the ProviderTable and the PhysicianTable. Together these cross reference the provider/biller relationship as well as keep track of actual accounting information for submission to accounts receivable.
4. The MetaDataConversionTable and its children are used to store specific pre-processing information regarding the special processing needs for specific providers. This includes the lexer to use, the conversion type, the names of the document fields in the header and their corresponding database fields.

Data Dictionary

The database entries in the preferred embodiment are defined according to the following data dictionary:

The DocMaster table is the main document table representing an instance of the transcript data being processed by the system. Prior to inserting a row of data into this table, the BillingCompID and ProviderID columns have already been identified. A unique integer value is assigned to the DocID column, the Primary Key that is used internally by the system to access the other relevant data members located in the other tables. The Sequence table is used to generate the next available DocID value. This is done to keep the generation of the unique key generic across the different RDBMS'. The following are the dependent tables and a short description of their content:

The LongDoc table contains the original transcript information in its original file format. The Primary key is composed of the DocID column. This table has a one-to-one relationship with the DocMaster table.

The DocHilite table contains all the highlight information used by the Coder Review Workstation application (CRW). The Primary Key is composed of the DocID, Field, and Position columns. The Position column is a counter, which is used to uniquely identify all the highlighted entries for a particular DocID.

The DocDetail table contains at least one instance of the EM component, Demographic, and Document flag data associated with a row in the DocMaster table. The DocID and Edited columns constitute the Primary Key for this table. The Edited column identifies multiple versions of the same DocID type data from different stages of the transformation process. The following are the possible values that currently can be assigned to the Edited column:

The data as it came out from the medical coding process (Edited=0).

The data edited by the Coder Review Workstation (Edited=1).

The data coming out of the Payer Rule engine. This is the customized, billing ready version that goes to the customer (Edited=2).

The DocCpt$_2$ DocIcd, and DocECode tables contain at least one instance of the ICD and CPT data that is initially generated by the medical coding process. The DocID, Edited, and Position columns constitute the Primary Key for this table.

The BillingMaster table is the main customer table. The BillingCompID column is the Primary Key for this table. The following are the dependent tables and a short description of what they contain:

The BillingPayables table contains the billing information for the particular Billing company. The Primary key is composed of the BillingCompID and Account columns. The Account column is a unique value used to identify the row in this table.

The ProviderMaster table contains the Provider specific information for each Billing company. The Primary key is composed of the BillingCompID and ProviderID columns. The ProviderID column is a unique value generated to identify each row in this table.

The Physician table contains the Physician information for a Provider serviced by a specific billing company. The Primary key is composed of the BillingCompID, ProviderID, and PhyCode columns. The PhyCode is predetermined.

The Patient table contains Patient information for a Provider serviced by a specific Billing Company. The Primary key is composed of the BillingCompID, ProviderID, and PatMRN columns.

The LUPayerClass table contains payer information for a provider serviced by a specific billing company. The Primary key is composed of the BillingCompID, ProviderID, and PayerCode columns. The PayerCode column values are defined by the specific Providers.

The ProviderConfig table contains information that the Converter module uses to identify the billing company and provider that the file being processed came from. The Primary key is composed of the Path column. This column contains the landing zone information for each provider.

The LexerFields table contains information that the Converter module uses to identify the provider specific field names to our system's naming convention. The Primary key is composed of the BillingCompID and ProviderID columns.

The other tables mostly fall in the Lookup Category. The following are the Lookup tables in the preferred schema:

The ObjectType table maintains information to uniquely identify the different lookup tables.

The LUDescriptions table contains lookup values of different types. The Primary key is composed of the ObjectID and Code columns. The Code column identifies the unique code within an object type. This table is dependent on the ObjectType table.

The LUReviewFlags table contains the lookup values used by the DocReviewFlags and CPTFlags lookup types. The Primary key is composed of the ObjectID and Flag columns. The Flag column identifies the unique flag code within an object type. This table is dependent on the ObjectType table.

The LUPayerRules table contains the rules used by the Billing Rules engine. The primary lookup column is the Category column. It can contain the PayerClass, ProviderID, or an <ALL> keyword. Although this table does not have a primary key, the Category field is indexed.

The LUCPT table is a lookup table for the CPT codes. The Primary key is the Code column.

The LUICD table is a lookup table for the ICD9 codes. The Primary key is the Code column.

Variants on the Current Implementation

The current implementation has been generally described in the context of three medical coding flow-through architectures: medical coding system 10; its associated medical coding process algorithms; and CRW operation. It should be appreciated that the combination of these architectures as proposed herein represents a substantial advance in the state-of-the-art in medical coding. The algorithms employed in medical coding system and coder review should be immediately understood by anyone practiced in the fields of data communications, data management and graphical user interfaces, in view of the above description. In addition, greater detail relating to such algorithms is set forth in the appendices referenced herein in terms of the objects that are used to construct them in accordance with a preferred implementation. The algorithms and architecture of the medical coding process, in particular, are described primarily in terms of its algorithms and the content of its databases.

Many other implementations of these ideas are possible in medical data management. Accordingly, the present invention provides a method for extracting billing, demographic and clinical information from computer readable physician notes. More particularly, the invention provides: organization and assessment of completeness for input notes and demographics; assignment of diagnosis, procedure and EM level codes based on the content of the note; resolution of the assigned codes with generic coding regulations, provider practices and payer specific billing requirements; and a flexible output for review and submission of claims.

An embodiment of the present invention has been described. Nevertheless, it will be understood that various modifications may be made without departing from the spirit and scope of the invention. For example, the use of single or networked computing environment, the use of the system by one or multiple users, the use of the system in batch or interactive mode, the use of scanned physician notes with forms recognition, and the use of the system for any variety of medical specialties are all within the spirit and scope of the invention. Moreover, as will be recognized by one skilled in the art, some of the processing steps are order-independent, and thus may be done in a sequence other than as described. Accordingly, it is to be understood that the invention is not to be limited by the specific illustrated embodiment, but only by the scope of the appended claims.

What is claimed is:

1. A method of automatically interpreting a transcribed note using vector processing to generate associated codes, the method comprising the steps of:
   (a) segmenting the transcribed note into a plurality of segments;
   (b) applying morphing, parsing and, semantic analysis to the segments to generate a normalized file having a standardized form with parse items, said semantic analysis comprising
      (1) identifying first type matches between parse items of the normalized file and a plurality of knowledge vectors, each of said knowledge vectors being manually-generated based on prior semantic knowledge and comprising data structure including
         one or more terms, each term having a weight based on the semantic category of the term, the weight being selected from a high weight, a low weight, and a middle weight,
         a high weight indicating that a term must be present in a parse item to get a match,
         a low weight indicating that a term, if present in a parse item, will improve a match, and
         a middle weight,
         wherein one or more of said knowledge vectors include a single term representing a numerical interval, wherein the numerical interval is represented in a vector through an interval index that map terms to semantically predefined intervals of acceptable values,
      the first type matches being indicative of associations to a single code, (2) generating associated codes at least on the basis of the first type matches and on the basis of natural language processing rules applied to the parse items; and (c) outputting the generated associated codes.

2. The method of claim 1, wherein the transcribed note is a physician note and the codes are diagnosis or procedure type codes.

3. The method of claim 1, wherein the transcribed note is a physician note and the codes are evaluation and management type codes.

4. The method of claim 1, wherein the transcribed note is a physician note, the method further comprising the step of extracting demographic information from the physician note.

5. The method of claim 1, wherein the transcribed note is a physician note, the method further comprising the step of extracting clinical information from the physician note.

6. The method of claim 1, wherein the transcribed note includes assertions by more than one person, the method further comprising the step of associating parse items to one of such persons.

7. The method of claim 1, further comprising the step of identifying second type matches between parse items and a plurality of semi-knowledge vectors, the second type matches each being indicative of associations to more than one code.

8. The method of claim 7, further comprising the step of flagging the normalized file when the parse items for which there is identified a second type match does not include a first type match to a standard knowledge vector.

9. The method of claim 8, further comprising the steps of:
(a) identifying a flagged normalized file; and
(b) generating a request for additional information on the basis of the second type match.

10. The method of claim 9, wherein the request for additional information involves downloading a record from a database.

11. The method of claim 9, wherein a response to the request for additional information involves human intervention.

12. The method of claim 10, wherein the request for additional information involves a specific request for information the response to which would result in a first type match with the parse item that caused the flagging.

13. A coding system for automatically interpreting a transcribed note to generate associated codes, comprising:
(a) a master import/export module for retrieving the transcribed note; and
(b) a filter module for processing text associated with the transcribed note to create a normalized file; and
(c) a natural language processing (NLP) engine using vector processing to associate from the normalized file a predetermined set of codes, wherein the NLP engine comprises:
(1) a module for morphing, parsing and semantically analyzing the structures and relations within the normalized file and identifying these in the form of parse items;
(2) a first vector matching module for identifying first type matches between the parse items and a plurality of knowledge vectors, each of said knowledge vectors being manually-generated based on prior semantic knowledge and comprising a data structure including
one or more terms, each term having a weight based on the semantic category of the term, the weight being selected from a high weight, a low weight, and a middle weight,
a high weight indicating that a term must be present in a parse item to get a match,
a low weight indicating that a term, if present in a parse item, will improve a match, and
a middle weight,
wherein one or more of said knowledge vectors include a single term representing a numerical interval, wherein the numerical interval is represented in a vector through an interval index that map terms to semantically predefined intervals of acceptable values,
the first type matches being indicative of associations to a single code; and
(3) a code generator for generating associated codes from the predetermined set of codes on the basis of the first type matches and on the basis of rules applied to the parse items.

14. The system of claim 13, wherein the transcribed note is a physician note and the codes are diagnosis or procedure type codes.

15. The system of claim 13, wherein the transcribed note is a physician note and the codes are evaluation and management type codes.

16. The system of claim 13, wherein the transcribed note is a physician note, the NLP engine further comprising a module for extracting demographic information from the physician note.

17. The system of claim 13, wherein the transcribed note is a physician note, the NLP engine further comprising a module for extracting clinical information from the physician note.

18. The system of claim 13, wherein the transcribed note includes assertions by more than one person, the system correlating parse items of the transcribed note to one such persons.

19. The system of claim 13, wherein the NLP engine further comprises a second matching module for identifying second type matches between the parse items and a plurality of semi-knowledge vectors, the second type matches each being indicative of associations to more than one code.

20. The system of claim 19, wherein the second matching module flags the normalized file in response to a second type match.

21. The system of claim 20, wherein the second matching module generates a request for additional information after the normalized file is flagged.

22. The system of claim 21, wherein the request for additional information involves downloading a record from a database.

23. The system of claim 21, wherein a response to the request for additional information involves human intervention.

24. The system of claim 23, further comprising a coder review workstation interface module, coupled to the second vector matching module, for transmitting the request for additional information to a human coder at a coder review workstation and for forwarding the response from the workstation to the NLP engine in real time.

25. The system of claim 22, wherein the request for additional information involves a specific request for information the response to which would result in a first type match with the parse item that caused the flagging.

26. The system of claim 13, further comprising a master process module for updating a record associated with the normalized file to generate a standardized report including the generated codes.

27. The system of claim 26, further comprising a payer process module coupled to the master process module for updating the record to include payer data information.

28. The system of claim 26, further comprising a client master module for exporting the record to a client billing system.

29. The system of claim 13, wherein the NLP engine performs vector processing on a weighted vector basis comprised of high and low weight elements.

30. The system of claim 13, further comprising a coder review workstation, the workstation including:

(a) an input device for inputting a non-transcribed note; and (b) a graphical user interface for viewing an encoded record of the non-transcribed note in real time.

31. The system of claim 30, wherein the input device is one of a keyboard, a mouse, an optical character recognizer, and an automatic speech recognition device.

32. The system of claim 13, further comprising a coder review workstation, the workstation including:

an input device for inputting a non-transcribed note;

a graphical user interface for displaying a template comprised of fields into which associated portions of the non-transcribed note is entered; and a template selector for allowing a human coder to select among a plurality of template note modules, each module corresponding to a predefined set of NLP rules for generating said codes.

33. A computer program, stored on a computer-readable medium, for interpreting a transcribed note using vector processing to generate associated codes, the computer program comprising instructions for causing a computer to:

segment the transcribed note to generate a plurality of segments;

morph, parse and semantically analyze the segments to generate a normalized file having a standardized form with parse items;

identify first type matches between parse items of the normalized file and a plurality of standard knowledge vectors, each of said knowledge vectors being manually-generated based on prior semantic knowledge and comprising a data structure including one or more terms, each term having a weight based on the semantic category of the term, the weight being selected from a high weight, a low weight, and a middle weight, a high weight indicating that a term must be present in a parse item to get a match, a low weight indicating that a term, if present in a parse item, will improve a match, and a middle weight, wherein one or more of said knowledge vectors include a single term representing a numerical interval, wherein the numerical interval is represented in a vector through an interval index that map terms to semantically predefined intervals of acceptable values, the first type matches being indicative of associations to a single code;

generate associated codes at least on the basis of the first type matches and on the basis of natural language processing rules applied to the parse items; and output the generated associated codes.

34. The computer program of claim 33, wherein the transcribed note is a physician note and the codes are diagnosis or procedure type codes.

35. The computer program of claim 33, wherein the transcribed note is a physician note and the codes are evaluation and management type codes.

36. The computer program of claim 33, wherein the transcribed note is a physician note the computer program further comprising instructions for extracting demographic information from the physician note.

37. The computer program of claim 33, wherein the transcribed note is a physician note, the computer program further comprising instructions for extracting clinical information from the physician note.

38. The computer program of claim 33, wherein the transcribed note includes assertions by more than one person, the computer program further comprising instructions for associating parse items to one of such persons.

39. The computer program of claim 33, further comprising instructions for identifying second type matches between parse items and a plurality of semi-knowledge vectors, the second type matches each being indicative of associations to more than one code.

40. The computer program of claim 39, further comprising instructions for flagging the normalized file when the parse items for which there is identified a second type match does not include a first type match to a standard knowledge vector.

41. The computer program of claim 40, further comprising instructions for:

(a) identifying a flagged normalized file; and (b) generating a request for additional information on the basis of the second type match.

42. The method of claim 1, wherein a plurality of said knowledge vectors have different lengths.

43. The method of claim 1, wherein said knowledge vectors are generated based on prior semantic knowledge.

44. The method of claim 43, wherein each of said knowledge vectors comprise a plurality of terms, each term having a weight based on the semantic category of the term.

45. The method of claim 1, wherein a plurality of said knowledge vectors are generated manually.

46. The method of claim 1, wherein terms assigned a high weight include terms denoting primary medical conditions and body parts.

47. The method of claim 1, wherein terms assigned a low weight include adjective denoting severity and quality and topological terms.

48. The method of claim 1, wherein said weights are stored separately from the knowledge vectors, wherein a first set of terms are stored as high weight terms and are applied as high weight terms consistently across the knowledge vectors, and wherein a second set of terms are stored as low weight terms and are applied as low weight terms consistently across the knowledge vectors.

49. The method in claim 1, wherein the weight of a term is resolved at run-time based on whether a term that is present in a source vector is also present in a target vector under comparison.

* * * * *